(12) United States Patent
Vrijbloed et al.

(10) Patent No.: US 11,407,799 B2
(45) Date of Patent: Aug. 9, 2022

(54) MUSCLE PERFORMANCE IMPROVEMENT COMPOUNDS COMPRISING C-TERMINUS AGRIN FRAGMENT AND AN ACTR2B INHIBITOR

(71) Applicant: PHARMAFOX THERAPEUTICS AG, Mohlin (CH)

(72) Inventors: Jan Willem Vrijbloed, Mohlin (CH); Marina Maria Boido, Nichelino (IT); Olena Butenko, Prague (CZ); Roberta Schellino, Turin (IT)

(73) Assignee: PHARMAFOX THERAPEUTICS AG, Mohlin (CH)

( * ) Notice: Subject to any disclaimer, the term of this patent is extended or adjusted under 35 U.S.C. 154(b) by 344 days.

(21) Appl. No.: 16/464,969

(22) PCT Filed: Nov. 28, 2017

(86) PCT No.: PCT/IB2017/057436
§ 371 (c)(1),
(2) Date: May 29, 2019

(87) PCT Pub. No.: WO2018/100483
PCT Pub. Date: Jun. 7, 2018

(65) Prior Publication Data
US 2021/0253654 A1    Aug. 19, 2021

(30) Foreign Application Priority Data

Nov. 29, 2016   (GB) ..................... 1620119

(51) Int. Cl.
*C07K 14/475*   (2006.01)
*C07K 14/71*   (2006.01)
*A61K 38/00*   (2006.01)

(52) U.S. Cl.
CPC ............ *C07K 14/475* (2013.01); *C07K 14/71* (2013.01); *A61K 38/00* (2013.01); *C07K 2317/70* (2013.01)

(58) Field of Classification Search
None
See application file for complete search history.

(56) References Cited

U.S. PATENT DOCUMENTS

| | | | | |
|---|---|---|---|---|
| 8,685,915 | B2 * | 4/2014 | Hettwer ................ | A61P 25/02 530/350 |
| 2006/0216279 | A1 | 9/2006 | Glass et al. | |
| 2008/0261879 | A1 * | 10/2008 | Melton ................. | A61K 38/185 514/8.3 |
| 2010/0004171 | A1 | 1/2010 | Bazan et al. | |
| 2010/0272734 | A1 * | 10/2010 | Berger ................. | A61K 45/06 435/69.6 |
| 2010/0316644 | A1 | 12/2010 | Seehra et al. | |
| 2010/0316645 | A1 * | 12/2010 | Imhof-Jung ............ | A61P 35/00 424/136.1 |
| 2011/0135638 | A1 | 6/2011 | Seehra et al. | |

FOREIGN PATENT DOCUMENTS

| | | | |
|---|---|---|---|
| CH | WO 2011/026615 | * 3/2011 | ............. A61K 38/17 |
| EP | 2 295 068 A1 | 3/2011 | |
| EP | 3 332 796 A1 | 6/2018 | |
| WO | WO 2004/039948 A2 | 5/2004 | |
| WO | WO 2008/030706 A2 | 3/2008 | |
| WO | WO 2008/100384 A2 | 8/2008 | |
| WO | WO 2010/125003 A1 | 11/2010 | |

OTHER PUBLICATIONS

Bhattacharya et al., PLoS ONE 12(3): e0171355. https://doi.org/10.1371/journal.pone.0171355 (Year: 2017).*
Fenton et al., Medicinal Chemistry Research (2020) 29:1133-1146 (Year: 2020).*
Piche-Nicholas et al., MAbs. 2018; 10: 81-94. doi: 10.1080/19420862.2017.1389355 (Year: 2018).*
Van Bulck et al., Int. J. Mol. Sci. 2019, 20, 719 doi:10.3390/ijms20030719 (Year: 2019).*
Corresponding International Application No. PCT/IB2017/057436—International Search Report, dated Jan. 31, 2018.
Corresponding International Application No. PCT/IB2017/057436—International Written Opinion, dated Jan. 31, 2018.
Corresponding Great Britain Application No. GB 1620119.6—Search Report, dated Jan. 9, 2017.
Shenhav Cohen et al., "Muscle wasting in disease: Molecular mechanisms and promising therapies", Nature Reviews Drug Discovery, vol. 14, No. 1, pp. 58-74, Dec. 31, 2014.
Francesco Curcio, et al., "Biomarkers in sarcopenia: A multifactorial approach", Experimental Gerontology, vol. 85, No. 8962, pp. 1-8, Sep. 12, 2016.

(Continued)

*Primary Examiner* — Christina M Borgeest
(74) *Attorney, Agent, or Firm* — Curatolo, Sidoti & Trillis Co., LPA; Salvatore A. Sidoti; Floyd Trillis, III

(57) ABSTRACT

A compound comprising at least two components, a first component being the nLG3 or (h)nLG3 domain from the C-terminus of mouse or human agrin, and at least one second component, selected from proteins or an antagonistic antibody that inhibit ActR2B-induced signaling activity in the presence of myostatin, the components being linked by means of linking entities.

Such compounds are effective treatments for neuromuscular diseases and problems.

4 Claims, 7 Drawing Sheets

Specification includes a Sequence Listing.

(56) References Cited

OTHER PUBLICATIONS

Toby Cornish, et al., "Globular domains of agrin are functional units that collaborate to induce acetylcholine receptor clustering", Journal of Cell Science, vol. 112, pp. 1213-1223, Mar. 23, 1999.

Trushar Patel, et al., "T-shaped arrangement of the recombinant agrin G3—IgG Fc protein", Protein Science, vol. 20, pp. 931-940, Mar. 29, 2011.

Eric Hoffman, et al., "Translating Mighty Mice into Neuromuscular Therapeutics—Is Bigger Muscle Better?", American Journal of Pathology, vol. 168, No. 6, Jun. 2006.

Markus Schuelke, et al., "Myostatin Mutation Associated with Gross Muscle Hypertrophy in a Child", The New England Journal of Medicine, vol. 350, No. 26, pp. 2682-2688, Jun. 24, 2004.

* cited by examiner

Lane 1: Fc-nLG3
Lane 2: nLG3-Fc
Lane 3: Fc-ActR
Lane 4: ActR-Fc
Lane 5: ActR-Fc-nLG3

Lane 6: (h)ActR-Fc
Lane 7: Fc-(h)nLG3
Lane 8: (h)ActR-Fc-(h)nLG3
Lane 9: (h)ActR-Fc-(h)LG3

Lane 10: ActRmAb
Lane 11: ActRmAb-(h)nLG3
Lane 12: MyomAb
Lane 13: MyomAb-(h)nLG3

SEQUENCE LISTING

<160> NUMBER OF SEQ ID NOS: 51

<210> SEQ ID NO 1
<211> LENGTH: 186
<212> TYPE: PRT
<213> ORGANISM: mouse

<400> SEQUENCE: 1

Ser Val Gly Asp Leu Glu Thr Leu Ala Phe Asp Gly Arg Thr Tyr Ile
1               5                   10                  15

Glu Tyr Leu Asn Ala Val Thr Glu Ser Glu Lys Ala Leu Gln Ser Asn
            20                  25                  30

His Phe Glu Leu Ser Leu Arg Thr Glu Ala Thr Gln Gly Leu Val Leu
            35                  40                  45

Trp Ile Gly Lys Val Gly Glu Arg Ala Asp Tyr Met Ala Leu Ala Ile
 50                  55                  60

Val Asp Gly His Leu Gln Leu Ser Tyr Asp Leu Gly Ser Gln Pro Val
 65                  70                  75                  80

Val Leu Arg Ser Thr Val Lys Val Asn Thr Asn Arg Trp Leu Arg Val
                 85                  90                  95

Arg Ala His Arg Glu His Arg Glu Gly Ser Leu Gln Val Gly Asn Glu
            100                 105                 110

Ala Pro Val Thr Gly Ser Ser Pro Leu Gly Ala Thr Gln Leu Asp Thr
            115                 120                 125

Asp Gly Ala Leu Trp Leu Gly Gly Leu Gln Lys Leu Pro Val Gly Gln
130                 135                 140

Ala Leu Pro Lys Ala Tyr Gly Thr Gly Phe Val Gly Cys Leu Arg Asp
145                 150                 155                 160

Val Val Val Gly His Arg Gln Leu His Leu Leu Glu Asp Ala Val Thr
                165                 170                 175

Lys Pro Glu Leu Arg Pro Cys Pro Thr Leu
            180                 185

<210> SEQ ID NO 2
<211> LENGTH: 8
<212> TYPE: PRT
<213> ORGANISM: mouse

<400> SEQUENCE: 2

Glu Leu Thr Asn Glu Ile Pro Ala
1               5

<210> SEQ ID NO 3
<211> LENGTH: 11
<212> TYPE: PRT
<213> ORGANISM: mouse

<400> SEQUENCE: 3

Pro Glu Thr Leu Asp Ser Arg Ala Leu Phe Ser
1               5                   10

<210> SEQ ID NO 4
<211> LENGTH: 19
<212> TYPE: PRT
<213> ORGANISM: mouse

<400> SEQUENCE: 4

Glu Leu Thr Asn Glu Ile Pro Ala Pro Glu Thr Leu Asp Ser Arg Ala
1               5                   10                  15

Leu Phe Ser

<210> SEQ ID NO 5
<211> LENGTH: 194
<212> TYPE: PRT
<213> ORGANISM: mouse

<400> SEQUENCE: 5

Ser Val Gly Asp Leu Glu Thr Leu Ala Phe Asp Gly Arg Thr Tyr Ile
1               5                   10                  15

Glu Tyr Leu Asn Ala Val Thr Glu Ser Glu Leu Thr Asn Glu Ile Pro
            20                  25                  30

-continued

Ala Glu Lys Ala Leu Gln Ser Asn His Phe Glu Leu Ser Leu Arg Thr
             35                  40                  45

Glu Ala Thr Gln Gly Leu Val Leu Trp Ile Gly Lys Val Gly Glu Arg
 50                  55                  60

Ala Asp Tyr Met Ala Leu Ala Ile Val Asp Gly His Leu Gln Leu Ser
 65                  70                  75                  80

Tyr Asp Leu Gly Ser Gln Pro Val Val Leu Arg Ser Thr Val Lys Val
                 85                  90                  95

Asn Thr Asn Arg Trp Leu Arg Val Arg Ala His Arg Glu His Arg Glu
             100                 105                 110

Gly Ser Leu Gln Val Gly Asn Glu Ala Pro Val Thr Gly Ser Ser Pro
         115                 120                 125

Leu Gly Ala Thr Gln Leu Asp Thr Asp Gly Ala Leu Trp Leu Gly Gly
 130                 135                 140

Leu Gln Lys Leu Pro Val Gly Gln Ala Leu Pro Lys Ala Tyr Gly Thr
145                 150                 155                 160

Gly Phe Val Gly Cys Leu Arg Asp Val Val Gly Arg His Arg Gln Leu
                 165                 170                 175

His Leu Leu Glu Asp Ala Val Thr Lys Pro Glu Leu Arg Pro Cys Pro
             180                 185                 190

Thr Leu

<210> SEQ ID NO 6
<211> LENGTH: 186
<212> TYPE: PRT
<213> ORGANISM: human

<400> SEQUENCE: 6

Ser Ala Gly Asp Val Asp Thr Leu Ala Phe Asp Gly Arg Thr Phe Val
 1               5                  10                  15

Glu Tyr Leu Asn Ala Val Thr Glu Ser Glu Lys Ala Leu Gln Ser Asn
             20                  25                  30

His Phe Glu Leu Ser Leu Arg Thr Glu Ala Thr Gln Gly Leu Val Leu
         35                  40                  45

Trp Ser Gly Lys Ala Thr Glu Arg Ala Asp Tyr Val Ala Leu Ala Ile
 50                  55                  60

Val Asp Gly His Leu Gln Leu Ser Tyr Asn Leu Gly Ser Gln Pro Val
 65                  70                  75                  80

Val Leu Arg Ser Thr Val Pro Val Asn Thr Asn Arg Trp Leu Arg Val
                 85                  90                  95

Val Ala His Arg Glu Gln Arg Glu Gly Ser Leu Gln Val Gly Asn Glu
             100                 105                 110

Ala Pro Val Thr Gly Ser Ser Pro Leu Gly Ala Thr Gln Leu Asp Thr
         115                 120                 125

Asp Gly Ala Leu Trp Leu Gly Gly Leu Pro Glu Leu Pro Val Gly Pro
 130                 135                 140

Ala Leu Pro Lys Ala Tyr Gly Thr Gly Phe Val Gly Cys Leu Arg Asp
145                 150                 155                 160

Val Val Val Gly Arg His Pro Leu His Leu Leu Glu Asp Ala Val Thr
                 165                 170                 175

Lys Pro Glu Leu Arg Pro Cys Pro Thr Pro
             180                 185

<210> SEQ ID NO 7
<211> LENGTH: 8

```
<212> TYPE: PRT
<213> ORGANISM: human

<400> SEQUENCE: 7

Glu Leu Ala Asn Glu Ile Pro Val
1               5

<210> SEQ ID NO 8
<211> LENGTH: 11
<212> TYPE: PRT
<213> ORGANISM: human

<400> SEQUENCE: 8

Pro Glu Thr Leu Asp Ser Gly Ala Leu His Ser
1               5                   10

<210> SEQ ID NO 9
<211> LENGTH: 19
<212> TYPE: PRT
<213> ORGANISM: human

<400> SEQUENCE: 9

Glu Leu Ala Asn Glu Ile Pro Val Pro Glu Thr Leu Asp Ser Gly Ala
1               5                   10                  15

Leu His Ser

<210> SEQ ID NO 10
<211> LENGTH: 194
<212> TYPE: PRT
<213> ORGANISM: human

<400> SEQUENCE: 10

Ser Ala Gly Asp Val Asp Thr Leu Ala Phe Asp Gly Arg Thr Phe Val
1               5                   10                  15

Glu Tyr Leu Asn Ala Val Thr Glu Ser Glu Leu Ala Asn Glu Ile Pro
                20                  25                  30

Val Glu Lys Ala Leu Gln Ser Asn His Phe Glu Leu Ser Leu Arg Thr
            35                  40                  45

Glu Ala Thr Gln Gly Leu Val Leu Trp Ser Gly Lys Ala Thr Glu Arg
        50                  55                  60

Ala Asp Tyr Val Ala Leu Ala Ile Val Asp Gly His Leu Gln Leu Ser
65                  70                  75                  80

Tyr Asn Leu Gly Ser Gln Pro Val Val Leu Arg Ser Thr Val Pro Val
                85                  90                  95

Asn Thr Asn Arg Trp Leu Arg Val Val Ala His Arg Glu Gln Arg Glu
            100                 105                 110

Gly Ser Leu Gln Val Gly Asn Glu Ala Pro Val Thr Gly Ser Ser Pro
        115                 120                 125

Leu Gly Ala Thr Gln Leu Asp Thr Asp Gly Ala Leu Trp Leu Gly Gly
    130                 135                 140

Leu Pro Glu Leu Pro Val Gly Pro Ala Leu Pro Lys Ala Tyr Gly Thr
145                 150                 155                 160

Gly Phe Val Gly Cys Leu Arg Asp Val Val Gly Arg His Pro Leu
                165                 170                 175

His Leu Leu Glu Asp Ala Val Thr Lys Pro Glu Leu Arg Pro Cys Pro
            180                 185                 190

Thr Pro
```

```
<210> SEQ ID NO 11
<211> LENGTH: 115
<212> TYPE: PRT
<213> ORGANISM: mouse

<400> SEQUENCE: 11

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Arg Asn Ser Ser Gly Thr Ile
        35                  40                  45

Glu Leu Val Lys Lys Gly Cys Trp Leu Asp Asp Phe Asn Cys Tyr Asp
50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Pro Gly Gly Pro Glu Val Thr Tyr Glu Pro Pro Pro Thr Ala Pro Thr
            100                 105                 110

Leu Leu Thr
        115

<210> SEQ ID NO 12
<211> LENGTH: 115
<212> TYPE: PRT
<213> ORGANISM: human

<400> SEQUENCE: 12

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Arg Asn Ser Ser Gly Thr Ile
        35                  40                  45

Glu Leu Val Lys Lys Gly Cys Trp Leu Asp Asp Phe Asn Cys Tyr Asp
50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Pro Thr Ala Pro Thr
            100                 105                 110

Leu Leu Thr
        115

<210> SEQ ID NO 13
<211> LENGTH: 15
<212> TYPE: PRT
<213> ORGANISM: artificial sequence
<220> FEATURE:
<223> OTHER INFORMATION: peptide

<400> SEQUENCE: 13

Gly Gly Gly Gly Ser Gly Gly Gly Ser Gly Gly Gly Gly Ser
1               5                   10                  15

<210> SEQ ID NO 14
<211> LENGTH: 227
```

<212> TYPE: PRT
<213> ORGANISM: human

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 435
<212> TYPE: PRT
<213> ORGANISM: artificial sequence
<220> FEATURE:
<223> OTHER INFORMATION: peptide

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile

```
            100                 105                 110
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Gly Ser Gly Gly Gly Gly Ser Gly Gly Gly
225                 230                 235                 240

Gly Ser Val Gly Asp Leu Glu Thr Leu Ala Phe Asp Gly Arg Thr Tyr
                245                 250                 255

Ile Glu Tyr Leu Asn Ala Val Thr Glu Ser Glu Leu Thr Asn Glu Ile
            260                 265                 270

Pro Ala Glu Lys Ala Leu Gln Ser Asn His Phe Glu Leu Ser Leu Arg
            275                 280                 285

Thr Glu Ala Thr Gln Gly Leu Val Leu Trp Ile Gly Lys Val Gly Glu
290                 295                 300

Arg Ala Asp Tyr Met Ala Leu Ala Ile Val Asp Gly His Leu Gln Leu
305                 310                 315                 320

Ser Tyr Asp Leu Gly Ser Gln Pro Val Val Leu Arg Ser Thr Val Lys
                325                 330                 335

Val Asn Thr Asn Arg Trp Leu Arg Val Arg Ala His Arg Glu His Arg
            340                 345                 350

Glu Gly Ser Leu Gln Val Gly Asn Glu Ala Pro Val Thr Gly Ser Ser
            355                 360                 365

Pro Leu Gly Ala Thr Gln Leu Asp Thr Asp Gly Ala Leu Trp Leu Gly
370                 375                 380

Gly Leu Gln Lys Leu Pro Val Gly Gln Ala Leu Pro Lys Ala Tyr Gly
385                 390                 395                 400

Thr Gly Phe Val Gly Cys Leu Arg Asp Val Val Val Gly His Arg Gln
                405                 410                 415

Leu His Leu Leu Glu Asp Ala Val Thr Lys Pro Glu Leu Arg Pro Cys
            420                 425                 430

Pro Thr Leu
            435

<210> SEQ ID NO 16
<211> LENGTH: 436
<212> TYPE: PRT
<213> ORGANISM: artificial sequence
<220> FEATURE:
<223> OTHER INFORMATION: peptide

<400> SEQUENCE: 16

Ser Val Gly Asp Leu Glu Thr Leu Ala Phe Asp Gly Arg Thr Tyr Ile
1               5                   10                  15

Glu Tyr Leu Asn Ala Val Thr Glu Ser Glu Leu Thr Asn Glu Ile Pro
```

-continued

```
            20                  25                  30
Ala Glu Lys Ala Leu Gln Ser Asn His Phe Glu Leu Ser Leu Arg Thr
        35                  40                  45

Glu Ala Thr Gln Gly Leu Val Leu Trp Ile Gly Lys Val Gly Glu Arg
    50                  55                  60

Ala Asp Tyr Met Ala Leu Ala Ile Val Asp Gly His Leu Gln Leu Ser
 65                  70                  75                  80

Tyr Asp Leu Gly Ser Gln Pro Val Val Leu Arg Ser Thr Val Lys Val
                85                  90                  95

Asn Thr Asn Arg Trp Leu Arg Val Arg Ala His Arg Glu His Arg Glu
            100                 105                 110

Gly Ser Leu Gln Val Gly Asn Glu Ala Pro Val Thr Gly Ser Ser Pro
        115                 120                 125

Leu Gly Ala Thr Gln Leu Asp Thr Asp Gly Ala Leu Trp Leu Gly Gly
    130                 135                 140

Leu Gln Lys Leu Pro Val Gly Gln Ala Leu Pro Lys Ala Tyr Gly Thr
145                 150                 155                 160

Gly Phe Val Gly Cys Leu Arg Asp Val Val Gly His Arg Gln Leu
                165                 170                 175

His Leu Leu Glu Asp Ala Val Thr Lys Pro Glu Leu Arg Pro Cys Pro
            180                 185                 190

Thr Leu Gly Gly Gly Ser Gly Gly Gly Ser Gly Gly Gly Gly
        195                 200                 205

Ser Asp Lys Thr His Thr Cys Pro Pro Cys Pro Ala Pro Glu Leu Leu
        210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys
        435
```

<210> SEQ ID NO 17
<211> LENGTH: 435
<212> TYPE: PRT
<213> ORGANISM: artificial sequence
<220> FEATURE:
<223> OTHER INFORMATION: peptide

<400> SEQUENCE: 17

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly Gly Gly Gly
225                 230                 235                 240

Gly Ser Ala Gly Asp Val Asp Thr Leu Ala Phe Asp Gly Arg Thr Phe
                245                 250                 255

Val Glu Tyr Leu Asn Ala Val Thr Glu Ser Glu Leu Ala Asn Glu Ile
            260                 265                 270

Pro Val Glu Lys Ala Leu Gln Ser Asn His Phe Glu Leu Ser Leu Arg
        275                 280                 285

Thr Glu Ala Thr Gln Gly Leu Val Leu Trp Ser Gly Lys Ala Thr Glu
    290                 295                 300

Arg Ala Asp Tyr Val Ala Leu Ala Ile Val Asp Gly His Leu Gln Leu
305                 310                 315                 320

Ser Tyr Asn Leu Gly Ser Gln Pro Val Val Leu Arg Ser Thr Val Pro
                325                 330                 335

Val Asn Thr Asn Arg Trp Leu Arg Val Ala His Arg Glu Gln Arg
            340                 345                 350

Glu Gly Ser Leu Gln Val Gly Asn Glu Ala Pro Val Thr Gly Ser Ser
        355                 360                 365
```

```
Pro Leu Gly Ala Thr Gln Leu Asp Thr Asp Gly Ala Leu Trp Leu Gly
        370                 375                 380

Gly Leu Pro Glu Leu Pro Val Gly Pro Ala Leu Pro Lys Ala Tyr Gly
385                 390                 395                 400

Thr Gly Phe Val Gly Cys Leu Arg Asp Val Val Gly Arg His Pro
                405                 410                 415

Leu His Leu Leu Glu Asp Ala Val Thr Lys Pro Glu Leu Arg Pro Cys
            420                 425                 430

Pro Thr Pro
        435

<210> SEQ ID NO 18
<211> LENGTH: 427
<212> TYPE: PRT
<213> ORGANISM: artificial sequence
<220> FEATURE:
<223> OTHER INFORMATION: peptide

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Ala Gly Asp Val Asp Thr Leu Ala Phe Asp Gly Arg Thr Phe
                245                 250                 255

Val Glu Tyr Leu Asn Ala Val Thr Ser Glu Lys Ala Leu Gln Ser
            260                 265                 270

Asn His Phe Glu Leu Ser Leu Arg Thr Glu Ala Thr Gln Gly Leu Val
        275                 280                 285
```

```
Leu Trp Ser Gly Lys Ala Thr Glu Arg Ala Asp Tyr Val Ala Leu Ala
        290                 295                 300

Ile Val Asp Gly His Leu Gln Leu Ser Tyr Asn Leu Gly Ser Gln Pro
305                 310                 315                 320

Val Val Leu Arg Ser Thr Val Pro Val Asn Thr Asn Arg Trp Leu Arg
                325                 330                 335

Val Val Ala His Arg Glu Gln Arg Glu Gly Ser Leu Gln Val Gly Asn
                340                 345                 350

Glu Ala Pro Val Thr Gly Ser Ser Pro Leu Gly Ala Thr Gln Leu Asp
            355                 360                 365

Thr Asp Gly Ala Leu Trp Leu Gly Gly Leu Pro Glu Leu Pro Val Gly
370                 375                 380

Pro Ala Leu Pro Lys Ala Tyr Gly Thr Gly Phe Val Gly Cys Leu Arg
385                 390                 395                 400

Asp Val Val Gly Arg His Pro Leu His Leu Leu Glu Asp Ala Val
                405                 410                 415

Thr Lys Pro Glu Leu Arg Pro Cys Pro Thr Pro
            420                 425
```

<210> SEQ ID NO 19
<211> LENGTH: 357
<212> TYPE: PRT
<213> ORGANISM: artificial sequence
<220> FEATURE:
<223> OTHER INFORMATION: peptide

<400> SEQUENCE: 19

```
Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
                20                  25                  30

Lys Arg Leu His Cys Tyr Ala Ser Trp Arg Asn Ser Ser Gly Thr Ile
            35                  40                  45

Glu Leu Val Lys Lys Gly Cys Trp Leu Asp Asp Phe Asn Cys Tyr Asp
50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Pro Gly Gly Pro Glu Val Thr Tyr Glu Pro Pro Pro Thr Ala Pro Thr
            100                 105                 110

Leu Leu Thr Gly Gly Gly Gly Ser Gly Gly Gly Ser Gly Gly Gly
            115                 120                 125

Gly Ser Asp Lys Thr His Thr Cys Pro Pro Cys Pro Ala Pro Glu Leu
        130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220
```

```
Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Glu Glu Met Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 20
<211> LENGTH: 357
<212> TYPE: PRT
<213> ORGANISM: artificial sequence
<220> FEATURE:
<223> OTHER INFORMATION: peptide

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220
```

```
Pro Gly Lys Gly Gly Gly Ser Gly Gly Gly Ser Gly Gly
225                 230                 235                 240

Gly Ser Glu Ala Glu Thr Arg Glu Cys Ile Tyr Tyr Asn Ala Asn Trp
            245                 250                 255

Glu Leu Glu Arg Thr Asn Gln Ser Gly Leu Glu Arg Cys Glu Gly Glu
        260                 265                 270

Gln Asp Lys Arg Leu His Cys Tyr Ala Ser Trp Arg Asn Ser Ser Gly
    275                 280                 285

Thr Ile Glu Leu Val Lys Lys Gly Cys Trp Leu Asp Asp Phe Asn Cys
290                 295                 300

Tyr Asp Arg Gln Glu Cys Val Ala Thr Glu Glu Asn Pro Gln Val Tyr
305                 310                 315                 320

Phe Cys Cys Cys Glu Gly Asn Phe Cys Asn Glu Arg Phe Thr His Leu
            325                 330                 335

Pro Glu Pro Gly Gly Pro Glu Val Thr Tyr Glu Pro Pro Thr Ala
        340                 345                 350

Pro Thr Leu Leu Thr
        355

<210> SEQ ID NO 21
<211> LENGTH: 357
<212> TYPE: PRT
<213> ORGANISM: artificial sequence
<220> FEATURE:
<223> OTHER INFORMATION: peptide

<400> SEQUENCE: 21

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Arg Asn Ser Ser Gly Thr Ile
        35                  40                  45

Glu Leu Val Lys Lys Gly Cys Trp Leu Asp Asp Phe Asn Cys Tyr Asp
    50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Thr Ala Pro Thr
            100                 105                 110

Leu Leu Thr Gly Gly Gly Gly Ser Gly Gly Gly Gly Ser Gly Gly Gly
        115                 120                 125

Gly Ser Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220
```

```
Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
        290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 22
<211> LENGTH: 565
<212> TYPE: PRT
<213> ORGANISM: artificial sequence
<220> FEATURE:
<223> OTHER INFORMATION: peptide

<400> SEQUENCE: 22

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Arg Asn Ser Ser Gly Thr Ile
        35                  40                  45

Glu Leu Val Lys Lys Gly Cys Trp Leu Asp Asp Phe Asn Cys Tyr Asp
50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Pro Gly Gly Pro Glu Val Thr Tyr Glu Pro Pro Pro Thr Ala Pro Thr
            100                 105                 110

Leu Leu Thr Gly Gly Gly Gly Ser Gly Gly Gly Ser Gly Gly Gly
        115                 120                 125

Gly Ser Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220
```

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Glu Glu Met Thr Lys Asn Gln
                260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
                340                 345                 350

Leu Ser Pro Gly Lys Gly Gly Gly Gly Ser Gly Gly Gly Gly Ser Gly
        355                 360                 365

Gly Gly Gly Ser Val Gly Asp Leu Glu Thr Leu Ala Phe Asp Gly Arg
370                 375                 380

Thr Tyr Ile Glu Tyr Leu Asn Ala Val Thr Glu Ser Glu Leu Thr Asn
385                 390                 395                 400

Glu Ile Pro Ala Glu Lys Ala Leu Gln Ser Asn His Phe Glu Leu Ser
            405                 410                 415

Leu Arg Thr Glu Ala Thr Gln Gly Leu Val Leu Trp Ile Gly Lys Val
                420                 425                 430

Gly Glu Arg Ala Asp Tyr Met Ala Leu Ala Ile Val Asp Gly His Leu
        435                 440                 445

Gln Leu Ser Tyr Asp Leu Gly Ser Gln Pro Val Val Leu Arg Ser Thr
    450                 455                 460

Val Lys Val Asn Thr Asn Arg Trp Leu Arg Val Arg Ala His Arg Glu
465                 470                 475                 480

His Arg Glu Gly Ser Leu Gln Val Gly Asn Glu Ala Pro Val Thr Gly
            485                 490                 495

Ser Ser Pro Leu Gly Ala Thr Gln Leu Asp Thr Asp Gly Ala Leu Trp
                500                 505                 510

Leu Gly Gly Leu Gln Lys Leu Pro Val Gly Gln Ala Leu Pro Lys Ala
        515                 520                 525

Tyr Gly Thr Gly Phe Val Gly Cys Leu Arg Asp Val Val Gly His
    530                 535                 540

Arg Gln Leu His Leu Leu Glu Asp Ala Val Thr Lys Pro Glu Leu Arg
545                 550                 555                 560

Pro Cys Pro Thr Leu
                565

<210> SEQ ID NO 23
<211> LENGTH: 565
<212> TYPE: PRT
<213> ORGANISM: artificial sequence
<220> FEATURE:
<223> OTHER INFORMATION: peptide

<400> SEQUENCE: 23

Glu Ala Glu Thr Arg Glu Cys Ile Tyr Tyr Asn Ala Asn Trp Glu Leu
1               5                   10                  15

-continued

```
Glu Arg Thr Asn Gln Ser Gly Leu Glu Arg Cys Glu Gly Glu Gln Asp
             20                  25                  30

Lys Arg Leu His Cys Tyr Ala Ser Trp Arg Asn Ser Ser Gly Thr Ile
         35                  40                  45

Glu Leu Val Lys Lys Gly Cys Trp Leu Asp Asp Phe Asn Cys Tyr Asp
     50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                 85                  90                  95

Ala Gly Gly Pro Glu Val Thr Tyr Glu Pro Pro Thr Ala Pro Thr
                100                 105                 110

Leu Leu Thr Gly Gly Gly Ser Gly Gly Gly Ser Gly Gly Gly
             115                 120                 125

Gly Ser Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
         180                 185                 190

Glu Val His Asn Ala Lys Thr Lys Pro Arg Glu Glu Gln Tyr Asn Ser
     195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
         260                 265                 270

Val Ser Leu Thr Cys Leu Val Lys Gly Phe Tyr Pro Ser Asp Ile Ala
     275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
         340                 345                 350

Leu Ser Pro Gly Lys Gly Gly Gly Ser Gly Gly Gly Gly Ser Gly
     355                 360                 365

Gly Gly Ser Ala Gly Asp Val Asp Thr Leu Ala Phe Asp Gly Arg
     370                 375                 380

Thr Phe Val Glu Tyr Leu Asn Ala Val Thr Glu Ser Glu Leu Ala Asn
385                 390                 395                 400

Glu Ile Pro Val Glu Lys Ala Leu Gln Ser Asn His Phe Glu Leu Ser
                405                 410                 415

Leu Arg Thr Glu Ala Thr Gln Gly Leu Val Leu Trp Ser Gly Lys Ala
         420                 425                 430
```

Thr Glu Arg Ala Asp Tyr Val Ala Leu Ala Ile Val Asp Gly His Leu
            435                 440                 445

Gln Leu Ser Tyr Asn Leu Gly Ser Gln Pro Val Val Leu Arg Ser Thr
        450                 455                 460

Val Pro Val Asn Thr Asn Arg Trp Leu Arg Val Val Ala His Arg Glu
465                 470                 475                 480

Gln Arg Glu Gly Ser Leu Gln Val Gly Asn Glu Ala Pro Val Thr Gly
                485                 490                 495

Ser Ser Pro Leu Gly Ala Thr Gln Leu Asp Thr Asp Gly Ala Leu Trp
            500                 505                 510

Leu Gly Gly Leu Pro Glu Leu Pro Val Gly Pro Ala Leu Pro Lys Ala
        515                 520                 525

Tyr Gly Thr Gly Phe Val Gly Cys Leu Arg Asp Val Val Gly Arg
        530                 535                 540

His Pro Leu His Leu Leu Glu Asp Ala Val Thr Lys Pro Glu Leu Arg
545                 550                 555                 560

Pro Cys Pro Thr Pro
                565

<210> SEQ ID NO 24
<211> LENGTH: 557
<212> TYPE: PRT
<213> ORGANISM: artificial sequence
<220> FEATURE:
<223> OTHER INFORMATION: peptide

<400> SEQUENCE: 24

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Arg Asn Ser Ser Gly Thr Ile
        35                  40                  45

Glu Leu Val Lys Lys Gly Cys Trp Leu Asp Asp Phe Asn Cys Tyr Asp
    50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Pro Thr Ala Pro Thr
            100                 105                 110

Leu Leu Thr Gly Gly Gly Gly Ser Gly Gly Gly Ser Gly Gly Gly Gly
        115                 120                 125

Gly Ser Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

```
Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
        245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys Gly Gly Gly Ser Gly Gly Gly Gly Ser Gly
        355                 360                 365

Gly Gly Gly Ser Ala Gly Asp Val Asp Thr Leu Ala Phe Asp Gly Arg
    370                 375                 380

Thr Phe Val Glu Tyr Leu Asn Ala Val Thr Glu Ser Glu Lys Ala Leu
385                 390                 395                 400

Gln Ser Asn His Phe Glu Leu Ser Leu Arg Thr Glu Ala Thr Gln Gly
                405                 410                 415

Leu Val Leu Trp Ser Gly Lys Ala Thr Glu Arg Ala Asp Tyr Val Ala
            420                 425                 430

Leu Ala Ile Val Asp Gly His Leu Gln Leu Ser Tyr Asn Leu Gly Ser
        435                 440                 445

Gln Pro Val Val Leu Arg Ser Thr Val Pro Val Asn Thr Asn Arg Trp
    450                 455                 460

Leu Arg Val Val Ala His Arg Glu Gln Arg Glu Gly Ser Leu Gln Val
465                 470                 475                 480

Gly Asn Glu Ala Pro Val Thr Gly Ser Ser Pro Leu Gly Ala Thr Gln
                485                 490                 495

Leu Asp Thr Asp Gly Ala Leu Trp Leu Gly Gly Leu Pro Glu Leu Pro
            500                 505                 510

Val Gly Pro Ala Leu Pro Lys Ala Tyr Gly Thr Gly Phe Val Gly Cys
        515                 520                 525

Leu Arg Asp Val Val Val Gly Arg His Pro Leu His Leu Leu Glu Asp
    530                 535                 540

Ala Val Thr Lys Pro Glu Leu Arg Pro Cys Pro Thr Pro
545                 550                 555

<210> SEQ ID NO 25
<211> LENGTH: 288
<212> TYPE: PRT
<213> ORGANISM: artificial sequence
<220> FEATURE:
<223> OTHER INFORMATION: peptide

<400> SEQUENCE: 25

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30
```

```
Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ser Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Gly Gly Gly
    210                 215                 220

Lys Lys Cys Leu Trp Asp Ser Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

<210> SEQ ID NO 26
<211> LENGTH: 530
<212> TYPE: PRT
<213> ORGANISM: artificial sequence
<220> FEATURE:
<223> OTHER INFORMATION: peptide

<400> SEQUENCE: 26

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110
```

-continued

```
Glu Cys Ala Leu Leu Lys Ala Arg Cys Lys Glu Gln Pro Glu Leu Glu
            115                 120                 125
Val Gln Tyr Gln Gly Lys Cys Lys Lys Thr Cys Arg Asp Val Phe Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Ser Ser Ser Glu Gln Tyr
                165                 170                 175
Leu Cys Gly Asn Asp Gly Val Thr Tyr Ser Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Gly Gly Gly
    210                 215                 220
Lys Lys Cys Leu Trp Asp Ser Lys Val Gly Arg Gly Arg Cys Ser Leu
225                 230                 235                 240
Cys Asp Glu Leu Cys Pro Asp Ser Lys Ser Asp Glu Pro Val Cys Ala
                245                 250                 255
Ser Asp Asn Ala Thr Tyr Ala Ser Glu Cys Ala Met Lys Glu Ala Ala
            260                 265                 270
Cys Ser Ser Gly Val Leu Leu Glu Val Lys His Ser Gly Ser Cys Asn
        275                 280                 285
Gly Gly Gly Ser Gly Gly Gly Ser Gly Gly Gly Ser Asp
    290                 295                 300
Lys Thr His Thr Cys Pro Pro Cys Pro Ala Pro Glu Leu Leu Gly Gly
305                 310                 315                 320
Pro Ser Val Phe Leu Phe Pro Pro Lys Pro Lys Asp Thr Leu Met Ile
                325                 330                 335
Ser Arg Thr Pro Glu Val Thr Cys Val Val Val Asp Val Ser His Glu
            340                 345                 350
Asp Pro Glu Val Lys Phe Asn Trp Tyr Val Asp Gly Val Glu Val His
        355                 360                 365
Asn Ala Lys Thr Lys Pro Arg Glu Glu Gln Tyr Asn Ser Thr Tyr Arg
    370                 375                 380
Val Val Ser Val Leu Thr Val Leu His Gln Asp Trp Leu Asn Gly Lys
385                 390                 395                 400
Glu Tyr Lys Cys Lys Val Ser Asn Lys Ala Leu Pro Ala Pro Ile Glu
                405                 410                 415
Lys Thr Ile Ser Lys Ala Lys Gly Gln Pro Arg Glu Pro Gln Val Tyr
            420                 425                 430
Thr Leu Pro Pro Ser Arg Glu Glu Met Thr Lys Asn Gln Val Ser Leu
        435                 440                 445
Thr Cys Leu Val Lys Gly Phe Tyr Pro Ser Asp Ile Ala Val Glu Trp
    450                 455                 460
Glu Ser Asn Gly Gln Pro Glu Asn Asn Tyr Lys Thr Thr Pro Pro Val
465                 470                 475                 480
Leu Asp Ser Asp Gly Ser Phe Phe Leu Tyr Ser Lys Leu Thr Val Asp
                485                 490                 495
Lys Ser Arg Trp Gln Gln Gly Asn Val Phe Ser Cys Ser Val Met His
            500                 505                 510
Glu Ala Leu His Asn His Tyr Thr Gln Lys Ser Leu Ser Leu Ser Pro
        515                 520                 525
Gly Lys
```

-continued

530

<210> SEQ ID NO 27
<211> LENGTH: 738
<212> TYPE: PRT
<213> ORGANISM: artificial sequence
<220> FEATURE:
<223> OTHER INFORMATION: peptide

<400> SEQUENCE: 27

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ser Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Gly Gly Gly
    210                 215                 220

Lys Lys Cys Leu Trp Asp Ser Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Gly Gly Gly Gly Ser Gly Gly Gly Ser Gly Gly Gly Gly Ser Asp
    290                 295                 300

Lys Thr His Thr Cys Pro Pro Cys Pro Ala Pro Glu Leu Leu Gly Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
            340                 345                 350

Asp Pro Glu Val Lys Phe Asn Trp Tyr Val Asp Gly Val Glu Val His
```

```
                355                 360                 365
Asn Ala Lys Thr Lys Pro Arg Glu Glu Gln Tyr Asn Ser Thr Tyr Arg
370                 375                 380
Val Val Ser Val Leu Thr Val Leu His Gln Asp Trp Leu Asn Gly Lys
385                 390                 395                 400
Glu Tyr Lys Cys Lys Val Ser Asn Lys Ala Leu Pro Ala Pro Ile Glu
            405                 410                 415
Lys Thr Ile Ser Lys Ala Lys Gly Gln Pro Arg Glu Pro Gln Val Tyr
            420                 425                 430
Thr Leu Pro Pro Ser Arg Glu Glu Met Thr Lys Asn Gln Val Ser Leu
        435                 440                 445
Thr Cys Leu Val Lys Gly Phe Tyr Pro Ser Asp Ile Ala Val Glu Trp
    450                 455                 460
Glu Ser Asn Gly Gln Pro Glu Asn Asn Tyr Lys Thr Thr Pro Pro Val
465                 470                 475                 480
Leu Asp Ser Asp Gly Ser Phe Phe Leu Tyr Ser Lys Leu Thr Val Asp
                485                 490                 495
Lys Ser Arg Trp Gln Gln Gly Asn Val Phe Ser Cys Ser Val Met His
            500                 505                 510
Glu Ala Leu His Asn His Tyr Thr Gln Lys Ser Leu Ser Leu Ser Pro
        515                 520                 525
Gly Lys Gly Gly Gly Gly Ser Gly Gly Gly Ser Gly Gly Gly Gly
    530                 535                 540
Ser Val Gly Asp Leu Glu Thr Leu Ala Phe Asp Gly Arg Thr Tyr Ile
545                 550                 555                 560
Glu Tyr Leu Asn Ala Val Thr Glu Ser Glu Leu Thr Asn Glu Ile Pro
                565                 570                 575
Ala Glu Lys Ala Leu Gln Ser Asn His Phe Glu Leu Ser Leu Arg Thr
            580                 585                 590
Glu Ala Thr Gln Gly Leu Val Leu Trp Ile Gly Lys Val Gly Glu Arg
        595                 600                 605
Ala Asp Tyr Met Ala Leu Ala Ile Val Asp Gly His Leu Gln Leu Ser
    610                 615                 620
Tyr Asp Leu Gly Ser Gln Pro Val Val Leu Arg Ser Thr Val Lys Val
625                 630                 635                 640
Asn Thr Asn Arg Trp Leu Arg Val Arg Ala His Arg Glu His Arg Glu
                645                 650                 655
Gly Ser Leu Gln Val Gly Asn Glu Ala Pro Val Thr Gly Ser Ser Pro
            660                 665                 670
Leu Gly Ala Thr Gln Leu Asp Thr Asp Gly Ala Leu Trp Leu Gly Gly
        675                 680                 685
Leu Gln Lys Leu Pro Val Gly Gln Ala Leu Pro Lys Ala Tyr Gly Thr
    690                 695                 700
Gly Phe Val Gly Cys Leu Arg Asp Val Val Val Gly His Arg Gln Leu
705                 710                 715                 720
His Leu Leu Glu Asp Ala Val Thr Lys Pro Glu Leu Arg Pro Cys Pro
                725                 730                 735
Thr Leu

<210> SEQ ID NO 28
<211> LENGTH: 445
<212> TYPE: PRT
<213> ORGANISM: artificial sequence
<220> FEATURE:
```

-continued

<223> OTHER INFORMATION: peptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 29
<211> LENGTH: 217
<212> TYPE: PRT
<213> ORGANISM: artificial sequence
<220> FEATURE:
<223> OTHER INFORMATION: peptide

<400> SEQUENCE: 29

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 30
<211> LENGTH: 653
<212> TYPE: PRT
<213> ORGANISM: artificial sequence
<220> FEATURE:
<223> OTHER INFORMATION: peptide

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45
```

-continued

```
Gly Thr Ile Asn Pro Val Ser Gly Thr Ser Tyr Ala Gln Lys Phe
         50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Gly Gly Trp Phe Asp Tyr Trp Gly Gln Gly Thr Leu Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys Gly Gly Gly
        435                 440                 445
Gly Ser Gly Gly Gly Gly Ser Gly Gly Gly Gly Ser Ala Gly Asp Val
450                 455                 460
```

```
Asp Thr Leu Ala Phe Asp Gly Arg Thr Phe Val Glu Tyr Leu Asn Ala
465                 470                 475                 480

Val Thr Glu Ser Glu Leu Ala Asn Glu Ile Pro Val Glu Lys Ala Leu
            485                 490                 495

Gln Ser Asn His Phe Glu Leu Ser Leu Arg Thr Glu Ala Thr Gln Gly
            500                 505                 510

Leu Val Leu Trp Ser Gly Lys Ala Thr Glu Arg Ala Asp Tyr Val Ala
        515                 520                 525

Leu Ala Ile Val Asp Gly Leu Gln Leu Ser Tyr Asn Leu Gly Ser
        530                 535                 540

Gln Pro Val Val Leu Arg Ser Thr Val Pro Val Asn Thr Asn Arg Trp
545                 550                 555                 560

Leu Arg Val Val Ala His Arg Glu Gln Arg Glu Gly Ser Leu Gln Val
            565                 570                 575

Gly Asn Glu Ala Pro Val Thr Gly Ser Ser Pro Leu Gly Ala Thr Gln
            580                 585                 590

Leu Asp Thr Asp Gly Ala Leu Trp Leu Gly Leu Pro Glu Leu Pro
        595                 600                 605

Val Gly Pro Ala Leu Pro Lys Ala Tyr Gly Thr Gly Phe Val Gly Cys
            610                 615                 620

Leu Arg Asp Val Val Gly Arg His Pro Leu His Leu Leu Glu Asp
625                 630                 635                 640

Ala Val Thr Lys Pro Glu Leu Arg Pro Cys Pro Thr Pro
                    645                 650

<210> SEQ ID NO 31
<211> LENGTH: 454
<212> TYPE: PRT
<213> ORGANISM: artificial sequence
<220> FEATURE:
<223> OTHER INFORMATION: peptide

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Lys Val
            20                  25                  30

Gly Ser Ser Val Ser Trp Ile Arg Gln Pro Pro Gly Lys Gly Leu Glu
        35                  40                  45

Trp Ile Gly His Ile Tyr Trp Asp Asp Lys Arg Leu Asn Pro Ser
    50                  55                  60

Leu Arg Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Arg Ala Ile Thr Thr Val Ile Gly Gly Thr Phe Asp
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175
```

```
Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 32
<211> LENGTH: 213
<212> TYPE: PRT
<213> ORGANISM: artificial sequence
<220> FEATURE:
<223> OTHER INFORMATION: peptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80
```

```
Asp Phe Ala Thr Tyr Tyr Cys Gln Gln Trp Tyr Leu His Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 33
<211> LENGTH: 662
<212> TYPE: PRT
<213> ORGANISM: artificial sequence
<220> FEATURE:
<223> OTHER INFORMATION: peptide

<400> SEQUENCE: 33

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Lys Val
            20                  25                  30

Gly Ser Ser Val Ser Trp Ile Arg Gln Pro Pro Gly Lys Gly Leu Glu
        35                  40                  45

Trp Ile Gly His Ile Tyr Trp Asp Asp Asp Lys Arg Leu Asn Pro Ser
    50                  55                  60

Leu Arg Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ala Ile Thr Thr Val Ile Gly Gly Gly Thr Phe Asp
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

-continued

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys Gly Gly Gly Ser Gly Gly Gly Ser
450                 455                 460

Gly Gly Gly Gly Ser Ala Gly Asp Val Asp Thr Leu Ala Phe Asp Gly
465                 470                 475                 480

Arg Thr Phe Val Glu Tyr Leu Asn Ala Val Thr Glu Ser Glu Leu Ala
            485                 490                 495

Asn Glu Ile Pro Val Glu Lys Ala Leu Gln Ser Asn His Phe Glu Leu
        500                 505                 510

Ser Leu Arg Thr Glu Ala Thr Gln Gly Leu Val Leu Trp Ser Gly Lys
    515                 520                 525

Ala Thr Glu Arg Ala Asp Tyr Val Ala Leu Ala Ile Val Asp Gly His
530                 535                 540

Leu Gln Leu Ser Tyr Asn Leu Gly Ser Gln Pro Val Val Leu Arg Ser
545                 550                 555                 560

Thr Val Pro Val Asn Thr Asn Arg Trp Leu Arg Val Val Ala His Arg
            565                 570                 575

Glu Gln Arg Glu Gly Ser Leu Gln Val Gly Asn Glu Ala Pro Val Thr
        580                 585                 590

Gly Ser Ser Pro Leu Gly Ala Thr Gln Leu Asp Thr Asp Gly Ala Leu
    595                 600                 605

Trp Leu Gly Gly Leu Pro Glu Leu Pro Val Gly Pro Ala Leu Pro Lys
610                 615                 620

Ala Tyr Gly Thr Gly Phe Val Gly Cys Leu Arg Asp Val Val Val Gly
625                 630                 635                 640

Arg His Pro Leu His Leu Leu Glu Asp Ala Val Thr Lys Pro Glu Leu
```

```
              645                 650                 655
Arg Pro Cys Pro Thr Pro
            660

<210> SEQ ID NO 34
<211> LENGTH: 1381
<212> TYPE: DNA
<213> ORGANISM: artificial sequence
<220> FEATURE:
<223> OTHER INFORMATION: expression vector

<400> SEQUENCE: 34
gcggccgcca tgaactttgg tctgaggctg attttctgg tgctgactct gaagggggtg      60
cagtgtgaca aacccacac ctgcccacct tgtcctgccc ctgaactgct gggaggacct     120
tctgtgtttc tgttcccacc aaaaccaaaa gataccctga tgatctctag aaccctgag    180 gtgacatgtg tggtggtgga tgtgtctcat gaggaccctg aggtcaaatt caactggtac    240
gtggatggag tggaagtcca caatgccaaa accaagccta gagaggaaca gtacaattca    300
acctacagag tggtcagtgt gctgactgtg ctgcatcagg attggctgaa tggcaaggaa    360
tacaagtgta agtctcaaa caaggccctg cctgctccaa ttgagaaaac aatctcaaag    420
gccaagggac agcctaggga accccaggtc tacaccctgc caccttcaag agaggaaatg    480
accaaaaacc aggtgtccct gacatgcctg gtcaaaggct ctaccccttc tgacattgct    540
gtggagtggg agtcaaatgg acagcctgag aacaactaca aacaaccccc cctgtgctg    600 gattctgatg gctctttctt tctgtactcc aaactgactg tggacaagtc tagatggcag    660
caggggaatg tctttctctg ctctgtcatg catgaggctc tgcataacca ctacactcag    720
aaatccctgt ctctgtctcc tggcaaaggc ggcggaggat ccgggggtgg gggaagcggc    780
ggaggaggta gtgtgggaga cctggagacc ctggcttttg acggcggac atacattgaa    840 tacctgaacg ctgtgaccga gagtgaactg actaatgaga tccctgcaga aaaggccctg    900
cagtcaaacc acttcgagct gtccctgagg accgaagcaa cacagggact ggtcctgtgg    960
atcggcaaag tgggagagcg agcagactac atggccctgg ctattgtgga tggccatctg   1020
cagctgtctt atgacctggg aagtcagcca gtggtcctga ggtctacagt caaagtgaac   1080
actaatagat ggctgaggggt gcgggctcac agagagcatc gcgaagggag cctgcaggtc   1140
ggtaatgaag caccagtgac cggctccagc cctctgggag caactcagct ggacaccgat   1200
ggggctctgt ggctgggagg actgcagaag ctgccagtcg ccaggctct gcccaaagca   1260 tacgggacag gttttgtggg gtgcctgcga gatgtggtcg tgggtcaccg tcagctgcac   1320
ctgctggagg acgctgtcac taagcctgaa ctgagacctt gccctaccct gtgataagct   1380
t                                                                   1381

<210> SEQ ID NO 35
<211> LENGTH: 1389
<212> TYPE: DNA
<213> ORGANISM: artificial sequence
<220> FEATURE:
<223> OTHER INFORMATION: expression vector

<400> SEQUENCE: 35
gcggccgcca tgaatttggg actgaggctg attttcctgg tgctgacct gaaaggcgtc      60 cagtgtagtg tgggagacct ggagaccctg gcttttgacg gcggacata cattgaatac     120 ctgaacgctg tgaccgagag tgaactgact aatgagatcc ctgcagaaaa ggccctgcag    180
```

| | |
|---|---|
| tcaaaccact tcgagctgtc cctgaggacc gaagcaacac agggactggt cctgtggatc | 240 |
| ggcaaagtgg gagagcgagc agactacatg gccctggcta ttgtggatgg ccatctgcag | 300 |
| ctgtcttatg acctgggaag tcagccagtg gtcctgaggt ctacagtcaa agtgaacact | 360 |
| aatagatggc tgagggtgcg ggctcacaga gagcatcgcg aagggagcct gcaggtcggt | 420 |
| aatgaagcac cagtgaccgg ctccagccct ctgggagcaa ctcagctgga caccgatggg | 480 |
| gctctgtggc tggaggact gcagaagctg ccagtcggcc aggctctgcc caaagcatac | 540 |
| gggacaggtt ttgtggggtg cctgcgagat gtggtcgtgg gtcaccgtca gctgcacctg | 600 |
| ctggaggacg ctgtcactaa gcctgaactg agaccttgcc ctaccctggg cggtggagga | 660 |
| tccggtggag gcggttctgg cggcggtggt agtgacaaaa cccacacctg cccaccttgt | 720 |
| cctgccctg aactgctggg aggaccttct gtgtttctgt tcccaccaaa accaaaagat | 780 |
| accctgatga tctctagaac ccctgaggtg acatgtgtg tggtggatgt gtctcatgag | 840 |
| gaccctgagg tcaaattcaa ctggtacgtg gatggagtgg aagtccacaa tgccaaaacc | 900 |
| aagcctagag aggaacagta caattcaacc tacagagtgt cagtgtgct gactgtgctg | 960 |
| catcaggatt ggctgaatgg caaggaatac aagtgtaaag tctcaaacaa ggccctgcct | 1020 |
| gctccaattg agaaaacaat ctcaaaggcc aagggacagc ctagggaacc ccaggtctac | 1080 |
| accctgccac cttcaagaga ggaaatgacc aaaaaccagg tgtccctgac atgcctggtc | 1140 |
| aaaggcttct accttctga cattgctgtg gagtgggagt caaatggaca gcctgagaac | 1200 |
| aactacaaaa caacccccc tgtgctggat tctgatggct ctttctttct gtactccaaa | 1260 |
| ctgactgtgg acaagtctag atggcagcag gggaatgtct ttcttgctc tgtcatgcat | 1320 |
| gaggctctgc ataaccacta cactcagaaa tccctgtctc tgtctcctgg caaatgatag | 1380 |
| taaaagctt | 1389 |

<210> SEQ ID NO 36
<211> LENGTH: 1379
<212> TYPE: DNA
<213> ORGANISM: artificial sequence
<220> FEATURE:
<223> OTHER INFORMATION: expression vector

<400> SEQUENCE: 36

| | |
|---|---|
| cggccgccat gaactttggt ctgaggctga ttttctggt gctgactctg aaggggtgc | 60 |
| agtgtgacaa aacccacacc tgcccacctt gtcctgcccc tgaactgctg ggaggacctt | 120 |
| ctgtgtttct gttcccacca aaaccaaaag atacccctgat gatctctaga accccctgagg | 180 |
| tgacatgtgt ggtggtggat gtgtctcatg aggaccctga ggtcaaattc aactggtacg | 240 |
| tggatggagt ggaagtccac aatgccaaaa ccaagcctag agaggaacag tacaattcaa | 300 |
| cctacagagt ggtcagtgtg ctgactgtgc tgcatcagga ttggctgaat ggcaaggaat | 360 |
| acaagtgtaa agtctcaaac aaggccctgc ctgctccaat tgagaaaaca atctcaaagg | 420 |
| ccaagggaca gcctagggaa ccccaggtct acaccctgcc accttcaaga gaggaaatga | 480 |
| ccaaaaacca ggtgtccctg acatgcctgg tcaaaggctt ctaccttct gacattgctg | 540 |
| tggagtggga gtcaaatgga cagcctgaga caactacaa acaacccccc ctgtgctgg | 600 |
| attctgatgg ctctttctt ctgtactcca aactgactgt ggacaagtct agatggcagc | 660 |
| aggggaatgt cttttcttgc tctgtcatgc atgaggctct gcataaccac tacactcaga | 720 |
| aatccctgtc tctgtctcct ggcaaaggcg gcggaggatc cggggtggg ggaagcggcg | 780 |
| gaggaggtag cgccggagac gtggacacat tggcatttga tggaaggaca tttgttgagt | 840 |

```
acctcaatgc ggtcacagaa agcgaactcg ccaacgaaat acctgtggag aaagccctac      900
agagtaatca cttcgagctg agtttaagaa ccgaggctac acagggccta gtgctttggt      960
ccggaaaggc caccgagcgg gctgactatg tggccctggc tatcgtggac ggtcatctgc     1020
agctgtcgta taatttgggc agccaaccag tggtcctcag atctactgtg cccgtcaaca     1080
caaatcgctg gcttagagtt gttgcacatc gcgagcaaag agagggcagc ttgcaagtgg     1140
ggaatgaagc ccctgtcacc ggaagcagcc ctctcggtgc cactcagttg gataccgatg     1200
gagccctgtg gcttggcggt ttgccagagt tgccagttgg ccctgctctg cccaaggcct     1260
atgggactgg cttcgttgga tgccttcgcg acgtggtggt cggccgtcac ccccttcacc     1320
ttctcgaaga tgcagtcacc aagccagaat acgcccttg tccaacccct tgataagct     1379
```

```
<210> SEQ ID NO 37
<211> LENGTH: 1357
<212> TYPE: DNA
<213> ORGANISM: artificial sequence
<220> FEATURE:
<223> OTHER INFORMATION: expression vector

<400> SEQUENCE: 37
```

```
gcggccgcca tgaactttgg tctgaggctg attttctgg tgctgactct gaaggggtg       60 cagtgtgaca aacccacac ctgcccacct tgtcctgccc ctgaactgct gggaggacct      120
tctgtgtttc tgttcccacc aaaaccaaaa gataccctga tgatctctag aacccctgag     180
gtgacatgtg tggtggtgga tgtgtctcat gaggaccctg aggtcaaatt caactggtac     240
gtggatggag tggaagtcca caatgccaaa accaagccta gagaggaaca gtacaattca     300
acctacagag tggtcagtgt gctgactgtg ctgcatcagg attggctgaa tggcaaggaa     360
tacaagtgta aagtctcaaa caaggccctg cctgctccaa ttgagaaaac aatctcaaag     420
gccaagggac agcctaggga accccaggtc tacaccctgc caccttcaag agaggaaatg     480
accaaaaacc aggtgtccct gacatgcctg gtcaaaggct tctacccttc tgacattgct     540
gtggagtggg agtcaaatgg acagcctgag aacaactaca aaacaacccc cctgtgctg      600 gattctgatg gctctttctt tctgtactcc aaactgactg tggacaagtc tagatggcag     660
caggggaatg tcttttcttg ctctgtcatg catgaggctc tgcataacca ctacactcag     720
aaatccctgt ctctgtctcc tggcaaaggc ggcgaggat ccggggtgg gggaagcggc      780 ggaggaggta gcgccggaga cgtggacaca ttggcatttg atggaaggac atttgttgag     840
tacctcaatg cggtcacaga aagcgagaaa gccctacaga gtaatcactt cgagctgagt     900
ttaagaaccg aggctacaca gggcctagtg ctttggtccg gaaaggccac cgagcgggct     960
gactatgtgg ccctggctat cgtggacggt catctgcagc tgtcgtataa tttgggcagc    1020
caaccagtgg tcctcagatc tactgtgccc gtcaacacaa atcgctggct tagagttgtt    1080
gcacatcgcg agcaaagaga gggcagcttg caagtgggga tgaagcccc tgtcaccgga    1140 agcagccctc tcggtgccac tcagttggat accgatggag ccctgtggct tggcggtttg    1200
ccagagttgc cagttggccc tgctctgccc aaggcctatg ggactggctt cgttggatgc    1260
cttcgcgacg tggtggtcgg ccgtcacccc cttcaccttc tcgaagatgc agtcaccaag    1320
ccagaattac gcccttgtcc aaccccttga taagctt                             1357
```

```
<210> SEQ ID NO 38
<211> LENGTH: 1147
<212> TYPE: DNA
```

<213> ORGANISM: artificial sequence
<220> FEATURE:
<223> OTHER INFORMATION: expression vector

<400> SEQUENCE: 38

| | |
|---|---|
| gcggccgcca tgaactttgg tctgaggctg attttttctgg tgctgactct gaagggggtg | 60 |
| cagtgtgaca aacccacac ctgcccacct tgtcctgccc ctgaactgct gggaggacct | 120 |
| tctgtgtttc tgttcccacc aaaaccaaaa gatacccctga tgatctctag aacccctgag | 180 |
| gtgacatgtg tggtggtgga tgtgtctcat gaggaccctg aggtcaaatt caactggtac | 240 |
| gtggatggag tggaagtcca caatgccaaa accaagccta gagaggaaca gtacaattca | 300 |
| acctacagag tggtcagtgt gctgactgtg ctgcatcagg attggctgaa tggcaaggaa | 360 |
| tacaagtgta aagtctcaaa caaggccctg cctgctccaa ttgagaaaac aatctcaaag | 420 |
| gccaagggac agcctaggga accccaggtc tacaccctgc caccttcaag agaggaaatg | 480 |
| accaaaaacc aggtgtccct gacatgcctg gtcaaaggct tctaccttc tgacattgct | 540 |
| gtggagtggg agtcaaatgg acagcctgag aacaactaca aaacaacccc ccctgtgctg | 600 |
| gattctgatg gctctttctt tctgtactcc aaactgactg tggacaagtc tagatggcag | 660 |
| caggggaatg tcttttcttg ctctgtcatg catgaggctc tgcataacca ctacactcag | 720 |
| aaatccctgt ctctgtctcc tggcaaaggc ggcggaggat ccggggtgg gggaagcggc | 780 |
| ggaggaggta gcgaagccga aactcgtgaa tgtatctact ataacgccaa ttgggagctg | 840 |
| gaaaggacta accagtctgg cctggagcgg tgtgagggag aacaggacaa gagactgcac | 900 |
| tgctacgctt cctggcgcaa ttccagcggg accattgagc tggtgaagaa aggttgttgg | 960 |
| ctggacgatt tcaactgtta cgatcgacag gaatgcgtgg caaccgagga aaatccccag | 1020 |
| gtctattttt gctgttgcga gggcaacttc tgcaatgaaa ggtttacaca tctgcctgag | 1080 |
| ccaggaggac ccgaagtgac ctacgaacca ccccctaccg cccctactct gctgacctga | 1140 |
| taagctt | 1147 |

<210> SEQ ID NO 39
<211> LENGTH: 1152
<212> TYPE: DNA
<213> ORGANISM: artificial sequence
<220> FEATURE:
<223> OTHER INFORMATION: expression vector

<400> SEQUENCE: 39

| | |
|---|---|
| gcggccgcca tgaattttgg actgaggctg atttttcctgg tgctgaccct gaaaggcgtc | 60 |
| cagtgtgaag ccgaaactcg tgaatgtatc tactataacg ccaattggga gctggaaagg | 120 |
| actaaccagt ctggcctgga gcggtgtgag ggagaacagg acaagagact gcactgctac | 180 |
| gcttcctggc gcaattccag cgggaccatt gagctggtga agaaaggttg ttggctggac | 240 |
| gatttcaact gttacgatcg acaggaatgc gtggcaaccg aggaaaatcc ccaggtctat | 300 |
| ttttgctgtt gcgagggcaa cttctgcaat gaaaggttta cacatctgcc tgagccagga | 360 |
| ggacccgaag tgacctacga accacccct accgcccta ctctgctgac cggcggtgga | 420 |
| ggatccggtg gaggcggttc tggcggcggt ggtagtgaca aacccacac ctgcccacct | 480 |
| tgtcctgccc ctgaactgct gggaggacct tctgtgtttc tgttcccacc aaaaccaaaa | 540 |
| gatacccctga tgatctctag aacccctgag gtgacatgtg tggtggtgga tgtgtctcat | 600 |
| gaggaccctg aggtcaaatt caactggtac gtggatggag tggaagtcca caatgccaaa | 660 |
| accaagccta gagaggaaca gtacaattca acctacagag tggtcagtgt gctgactgtg | 720 |

```
ctgcatcagg attggctgaa tggcaaggaa tacaagtgta aagtctcaaa caaggccctg      780
cctgctccaa ttgagaaaac aatctcaaag gccaagggac agcctaggga accccaggtc      840
tacaccctgc caccttcaag agaggaaatg accaaaaacc aggtgtccct gacatgcctg      900
gtcaaaggct tctaccctte tgacattgct gtggagtggg agtcaaatgg acagcctgag      960
aacaactaca aaacaacccc ccctgtgctg gattctgatg gctctttctt tctgtactcc     1020
aaactgactg tggacaagtc tagatggcag caggggaatg tcttttcttg ctctgtcatg     1080
catgaggctc tgcataacca ctacactcag aaatccctgt ctctgtctcc tggcaaatga     1140
tagtaaaagc tt                                                         1152
```

<210> SEQ ID NO 40
<211> LENGTH: 1152
<212> TYPE: DNA
<213> ORGANISM: artificial sequence
<220> FEATURE:
<223> OTHER INFORMATION: expression vector

<400> SEQUENCE: 40

```
gcggccgcca tgaattttgg actgaggctg attttcctgg tgctgaccct gaaaggcgtc       60
cagtgtgaag ccgaaactcg tgaatgtatc tactataacg ccaattggga gctggaaagg      120
actaaccagt ctggcctgga gcggtgtgag ggagaacagg acaagagact gcactgctac      180
gcttcctggc gcaattccag cgggaccatt gagctggtga agaaaggttg ttggctggac      240
gatttcaact gttacgatcg acaggaatgc gtggcaaccg aggaaaatcc ccaggtctat      300
ttttgctgtt gcgagggcaa cttctgcaat gaaaggttta cacatctgcc tgaggcagga      360
ggacccgaag tgacctacga accaccccct accgccccta ctctgctgac cggcggtgga      420
ggatccggtg gaggcggttc tggcggcggt ggtagtgaca aaacccacac ctgcccacct      480
tgtcctgccc ctgaactgct gggaggacct tctgtgtttc tgttcccacc aaaaccaaaa      540
gataccctga tgatctctag aacccctgag gtgacatgtg tggtggtgga tgtgtctcat      600
gaggaccctg aggtcaaatt caactggtac gtggatggag tggaagtcca caatgccaaa      660
accaagccta gagaggaaca gtacaattca acctacagag tggtcagtgt gctgactgtg      720
ctgcatcagg attggctgaa tggcaaggaa tacaagtgta aagtctcaaa caaggccctg      780
cctgctccaa ttgagaaaac aatctcaaag gccaagggac agcctaggga accccaggtc      840
tacaccctgc caccttcaag agaggaaatg accaaaaacc aggtgtccct gacatgcctg      900
gtcaaaggct tctaccctte tgacattgct gtggagtggg agtcaaatgg acagcctgag      960
aacaactaca aaacaacccc ccctgtgctg gattctgatg gctctttctt tctgtactcc     1020
aaactgactg tggacaagtc tagatggcag caggggaatg tcttttcttg ctctgtcatg     1080
catgaggctc tgcataacca ctacactcag aaatccctgt ctctgtctcc tggcaaatga     1140
tagtaaaagc tt                                                         1152
```

<210> SEQ ID NO 41
<211> LENGTH: 1770
<212> TYPE: DNA
<213> ORGANISM: artificial sequence
<220> FEATURE:
<223> OTHER INFORMATION: expression vector

<400> SEQUENCE: 41

```
cggccgccat gaattttgga ctgaggctga ttttcctggt gctgaccctg aaaggcgtcc       60
```

```
agtgtgaagc cgaaactcgt gaatgtatct actataacgc caattgggag ctggaaagga      120
ctaaccagtc tggcctggag cggtgtgagg gagaacagga caagagactg cactgctacg      180
cttcctggcg caattccagc gggaccattg agctggtgaa gaaaggttgt tggctggacg      240
atttcaactg ttacgatcga caggaatgcg tggcaaccga ggaaaatccc caggtctatt      300
tttgctgttg cgagggcaac ttctgcaatg aaaggtttac acatctgcct gagccaggag      360
gacccgaagt gacctacgaa ccaccccta ccgcccctac tctgctgacc ggcggtggag       420
gatccggtgg aggcggttct ggcggcggtg gtagtgacaa aacccacacc tgcccacctt      480
gtcctgcccc tgaactgctg ggaggacctt ctgtgtttct gttcccacca aaaccaaaag      540
ataccctgat gatctctaga acccctgagg tgacatgtgt ggtggtggat gtgtctcatg      600
aggaccctga ggtcaaattc aactggtacg tggatggagt ggaagtccac aatgccaaaa      660
ccaagcctag agaggaacag tacaattcaa cctacagagt ggtcagtgtg ctgactgtgc      720
tgcatcagga ttggctgaat ggcaaggaat acaagtgtaa agtctcaaac aaggccctgc      780
ctgctccaat tgaaaaaaca atctcaaagg ccaagggaca gccctaggaa ccccaggtct      840
acaccctgcc accttcaaga gaggaaatga ccaaaaacca ggtgtccctg acatgcctgg      900
tcaaaggctt ctacccttct gacattgctg tggagtggga gtcaaatgga cagcctgaga      960
acaactacaa aacaaccccc cctgtgctgg attctgatgg ctctttcttt ctgtactcca     1020
aactgactgt ggacaagtct agatggcagc agggaatgc ttttcttgc tctgtcatgc      1080 atgaggctct gcataaccac tacactcaga atccctgtc tctgtctcct ggcaaaggcg      1140
gcggaggatc cggggtggg ggaagcggcg gaggaggtag tgtgggagac ctggagaccc      1200
tggcttttga cgggcggaca tacattgaat acctgaacgc tgtgaccgag agtgaactga     1260
ctaatgagat ccctgcagaa aaggccctgc agtcaaacca cttcgagctg tccctgagga     1320
ccgaagcaac acagggactg gtcctgtgga tcggcaaagt gggagagcga gcagactaca     1380
tggccctggc tattgtggat ggccatctgc agctgtctta tgacctggga agtcagccag     1440
tggtcctgag gtctacagtc aaagtgaaca ctaatagatg gctgagggtg cgggctcaca     1500
gagagcatcg cgaagggagc ctgcaggtcg gtaatgaagc accagtgacc ggctccagcc     1560
ctctgggagc aactcagctg gacaccgatg gggctctgtg gctgggagga ctgcagaagc     1620
tgccagtcgg ccaggctctg cccaaagcat acgggacagg ttttgtgggg tgcctgcgag     1680
atgtggtcgt gggtcaccgt cagctgcacc tgctgggaga cgctgtcact aagcctgaac     1740
tgagaccttg ccctaccctg tgataagctt                                       1770
```

<210> SEQ ID NO 42
<211> LENGTH: 1771
<212> TYPE: DNA
<213> ORGANISM: artificial sequence
<220> FEATURE:
<223> OTHER INFORMATION: expression vector

<400> SEQUENCE: 42

```
gcggccgcca tgaattttgg actgaggctg attttcctgg tgctgacccl gaaaggcgtc       60 cagtgtgaag ccgaaactcg tgaatgtatc tactataacg ccaattggga gctggaaagg      120
actaaccagt ctggcctgga gcggtgtgag ggagaacagg acaagagact gcactgctac      180
gcttcctggc gcaattccag cgggaccatt gagctggtga agaaaggttg ttggctggac      240
gatttcaact gttacgatcg acaggaatgc gtggcaaccg aggaaaatcc ccaggtctat      300
ttttgctgtt gcgagggcaa cttctgcaat gaaaggttta cacatctgcc tgaggcagga      360
```

```
ggacccgaag tgacctacga accacccct accgcccta ctctgctgac cggcggtgga      420
ggatccggtg gaggcggttc tggcggcggt ggtagtgaca aaacccacac ctgcccacct      480
tgtcctgccc ctgaactgct gggaggacct tctgtgtttc tgttcccacc aaaaccaaaa      540 gatacccctga tgatctctag aaccctgag gtgacatgtg tggtggtgga tgtgtctcat       600
gaggaccctg aggtcaaatt caactggtac gtggatggag tggaagtcca caatgccaaa       660
accaagccta gagggaaca gtacaattca acctacagag tggtcagtgt gctgactgtg       720
ctgcatcagg attggctgaa tggcaaggaa tacaagtgta agtctcaaa caaggccctg       780 cctgctccaa ttgagaaaac aatctcaaag gccaagggac agcctaggga accccaggtc       840
tacaccctgc caccttcaag agaggaaatg accaaaaacc aggtgtccct gacatgcctg       900
gtcaaaggct ctaccccttc tgacattgct gtggagtggg agtcaaatgg acagcctgag       960
aacaactaca aaacaacccc ccctgtgctg gattctgatg gctcttctct tctgtactcc      1020
aaactgactg tggacaagtc tagatggcag caggggaatg tcttttcttg ctctgtcatg      1080
catgaggctc tgcataacca ctacactcag aaatccctgt ctctgtctcc tggcaaaggc      1140
ggcggaggat ccgggggtgg gggaagcggc ggaggaggta cgccggaga cgtggacaca      1200 ttggcatttg atggaaggac atttgttgag tacctcaatg cggtcacaga aagcgaactc      1260
gccaacgaaa tacctgtgga gaaagcccta cagagtaatc acttcgagct gagtttaaga      1320
accgaggcta cacagggcct agtgctttgg tccggaaagg ccaccgagcg ggctgactat      1380
gtggccctgg ctatcgtgga cggtcatctg cagctgtcgt ataattttgg cagccaacca      1440
gtggtcctca gatctactgt gcccgtcaac acaaatcgct ggcttagagt tgttgcacat      1500
cgcgagcaaa gagagggcag cttgcaagtg gggaatgaag ccctgtcac cggaagcagc      1560 cctctcggtg ccactcagtt ggataccgat ggagccctgt ggcttggcgg tttgccagag      1620
ttgccagttg gccctgctct gcccaaggcc tatgggactg gcttcgttgg atgccttcgc      1680
gacgtggtgg tcggccgtca ccccttcac cttctcgaag atgcagtcac caagccagaa      1740 ttacgcccctt gtccaacccc ttgataagct t                                    1771
```

<210> SEQ ID NO 43
<211> LENGTH: 1747
<212> TYPE: DNA
<213> ORGANISM: artificial sequence
<220> FEATURE:
<223> OTHER INFORMATION: expression vector

<400> SEQUENCE: 43

```
gcggccgcca tgaattttgg actgaggctg attttcctgg tgctgacccct gaaaggcgtc       60 cagtgtgaag ccgaaactcg tgaatgtatc tactataacg ccaattggga gctggaaagg      120
actaaccagt ctggcctgga gcggtgtgag ggagaacagg acaagagact gcactgctac      180
gcttcctggc gcaattccag cggggaccatt gagctggtga agaaaggttg ttggctggac      240
gatttcaact gttacgatcg acaggaatgc gtggcaaccg aggaaaatcc ccaggtctat      300
ttttgctgtt gcgagggcaa cttctgcaat gaaaggtta cacatctgcc tgaggcagga      360
ggacccgaag tgacctacga accacccct accgcccta ctctgctgac cggcggtgga      420
ggatccggtg gaggcggttc tggcggcggt ggtagtgaca aaacccacac ctgcccacct      480
tgtcctgccc ctgaactgct gggaggacct tctgtgtttc tgttcccacc aaaaccaaaa      540 gatacccctga tgatctctag aaccctgag gtgacatgtg tggtggtgga tgtgtctcat       600
```

```
gaggaccctg aggtcaaatt caactggtac gtggatggag tggaagtcca caatgccaaa      660
accaagccta gagaggaaca gtacaattca acctacagag tggtcagtgt gctgactgtg      720
ctgcatcagg attggctgaa tggcaaggaa tacaagtgta aagtctcaaa caaggccctg      780
cctgctccaa ttgagaaaac aatctcaaag gccaagggac agcctaggga accccaggtc      840
tacaccctgc caccttcaag agaggaaatg accaaaaacc aggtgtccct gacatgcctg      900
gtcaaaggct tctacccttc tgacattgct gtggagtggg agtcaaatgg acagcctgag      960
aacaactaca aacaacccc ccctgtgctg gattctgatg gctctttctt tctgtactcc      1020
aaactgactg tggacaagtc tagatggcag caggggaatg tcttttcttg ctctgtcatg      1080
catgaggctc tgcataacca ctacactcag aaatccctgt ctctgtctcc tggcaaaggc      1140
ggcggaggat ccggggggtgg gggaagcggc ggaggaggta cgccggaga cgtggacaca      1200 ttggcatttg atggaaggac atttgttgag tacctcaatg cggtcacaga aagcgagaaa      1260
gccctacaga gtaatcactt cgagctgagt ttaagaaccg aggctacaca gggcctagtg      1320
ctttggtccg gaaaggccac cgagcgggct gactatgtgg ccctggctat cgtggacggt      1380
catctgcagc tgtcgtataa tttgggcagc caaccagtgg tcctcagatc tactgtgccc      1440
gtcaacacaa atcgctggct tagagttgtt gcacatcgcg agcaaagaga gggcagcttg      1500
caagtgggga tgaagccccc tgtcaccgga agcagccctc tcggtgccac tcagttggat      1560
accgatggag ccctgtggct tggcggtttg ccagagttgc cagttggccc tgctctgccc      1620
aaggcctatg ggactggctt cgttggatgc cttcgcgacg tggtggtcgg ccgtcacccc      1680
cttcaccttc tcgaagatgc agtcaccaag ccagaattac gcccttgtcc aaccccttga      1740
taagctt                                                               1747

<210> SEQ ID NO 44
<211> LENGTH: 732
<212> TYPE: DNA
<213> ORGANISM: artificial sequence
<220> FEATURE:
<223> OTHER INFORMATION: expression vector

<400> SEQUENCE: 44
gcggccgcca tgaattttgg actgaggctg attttcctgg tgctgaccct gaaaggcgtc       60
cagtgtcagt ccgccctaac ccagcccgca agcgtttcag gttctcccgg gcagagtatt      120
acaatcagtt gcaccgggac ctccagcgat gtcggcagct ataactacgt gaattggtac      180
cagcaacatc ccggcaaagc acctaagctc atgatctatg gtgtttccaa cgacccagc       240 ggagtgtcca acaggttttc tggatccaaa tcgggcaata cagccagcct gaccatttcg      300
gggctacaag cggaggatga agcagactac tactgtggaa cttttcgcag cgggtcctac      360
tatggggtgt tcggaggcgg caccaagctc acggtgttag gtcagccaaa agcggcgcca      420
tccgtcaccc tgttccctcc ctcatccgag gaactgcagg ccaataaggc tacactggtc      480
tgtctgatta gcgacttcta ccctgggcc gtgactgtgg cttggaaagc cgattcttct      540
cccgtgaaag ctggagtgga acaaccacc ccctctaaac agagcaacaa caaatacgct      600
gcctcttcat acctgtccct gacccctgaa cagtggaaat ctcaccggtc ttactcatgc      660
caggtgacac acgagggatc aactgtggag aaaaccgtgg ctcctaccga atgttcatga      720
tagtaaaagc tt                                                          732

<210> SEQ ID NO 45
<211> LENGTH: 1416
```

<212> TYPE: DNA
<213> ORGANISM: artificial sequence
<220> FEATURE:
<223> OTHER INFORMATION: expression vector

<400> SEQUENCE: 45

| | | | | | |
|---|---|---|---|---|---|
| gcggccgcca | tgaattttgg | actgaggctg | attttcctgg | tgctgaccct | gaaaggcgtc | 60 |
| cagtgtcagg | ttcagttggt | tcagtcaggt | gccgaggtga | agaagcctgg | ggcttccgtg | 120 |
| aaggtttctt | gcaaagcctc | cggctacaca | tttacttcca | gctatataaa | ctgggtgcga | 180 |
| caggctcctg | gtcagggact | cgaatggatg | ggaacaataa | accccgtgtc | agggtccact | 240 |
| tcatacgctc | agaagtttca | gggccgggta | acaatgacca | gagatacctc | aatctccacc | 300 |
| gcctacatgg | aactgagtcg | ccttcggtca | gatgacactg | ccgtgtatta | ctgtgcaagg | 360 |
| gggggctggt | tgattactg | gggacagggt | actctggtta | ctgtctcgag | cgctagcaca | 420 |
| aagggcccta | gtgtgtttcc | tctggctccc | tcttccaaat | ccacttctgg | tggcactgct | 480 |
| gctctgggat | gctggtgaa | ggattacttt | cctgaacctg | tgactgtctc | atggaactct | 540 |
| ggtgctctga | cttctggtgt | ccacactttc | cctgctgtgc | tgcagtctag | tggactgtac | 600 |
| tctctgtcat | ctgtggtcac | tgtgccctct | tcatctctgg | gaacccagac | ctacatttgt | 660 |
| aatgtgaacc | acaaccatc | caacactaaa | gtggacaaaa | agtggaacc | caaatcctgt | 720 |
| gacaaaaccc | acacctgccc | accttgtcct | gcccctgaac | tgctgggagg | accttctgtg | 780 |
| tttctgttcc | cccccaaacc | aaaggatacc | ctgatgatct | ctagaacccc | tgaggtgaca | 840 |
| tgtgtggtgg | tggatgtgtc | tcatgaggac | cctgaggtca | aattcaactg | gtacgtggat | 900 |
| ggagtggaag | tccacaatgc | caaaaccaag | cctagagagg | aacagtacaa | ttcaacctac | 960 |
| agagtggtca | gtgtgctgac | tgtgctgcat | caggattggc | tgaatggcaa | ggaatacaag | 1020 |
| tgtaaagtct | caaacaaggc | cctgcctgct | ccaattgaga | aaacaatctc | aaaggccaag | 1080 |
| ggacagccta | gggaaccca | ggtctacacc | ctgccacctt | caagagagga | aatgaccaaa | 1140 |
| aaccaggtgt | ccctgacatg | cctggtcaaa | ggcttctacc | cttctgacat | tgctgtggag | 1200 |
| tgggagtcaa | atggacagcc | tgagaacaac | tacaaaacaa | ccccccctgt | gctggattct | 1260 |
| gatggctctt | tctttctgta | ctccaaactg | actgtggaca | agtctagatg | gcagcagggg | 1320 |
| aatgtctttt | cttgctctgt | catgcatgag | gctctgcata | accactacac | tcagaaatcc | 1380 |
| ctgtctctgt | ctcccgggaa | atgatagtaa | aagctt | | | 1416 |

<210> SEQ ID NO 46
<211> LENGTH: 2035
<212> TYPE: DNA
<213> ORGANISM: artificial sequence
<220> FEATURE:
<223> OTHER INFORMATION: expression vector

<400> SEQUENCE: 46

| | | | | | |
|---|---|---|---|---|---|
| gcggccgcca | tgaattttgg | actgaggctg | attttcctgg | tgctgaccct | gaaaggcgtc | 60 |
| cagtgtcagg | ttcagttggt | tcagtcaggt | gccgaggtga | agaagcctgg | ggcttccgtg | 120 |
| aaggtttctt | gcaaagcctc | cggctacaca | tttacttcca | gctatataaa | ctgggtgcga | 180 |
| caggctcctg | gtcagggact | cgaatggatg | ggaacaataa | accccgtgtc | agggtccact | 240 |
| tcatacgctc | agaagtttca | gggccgggta | acaatgacca | gagatacctc | aatctccacc | 300 |
| gcctacatgg | aactgagtcg | ccttcggtca | gatgacactg | ccgtgtatta | ctgtgcaagg | 360 |
| gggggctggt | tgattactg | gggacagggt | actctggtta | ctgtctcgag | cgctagcaca | 420 |

```
aagggccc ta gtgtgttt cc tctggctccc tcttccaaat ccacttctgg tggcactgct      480
gctctgggat gcctggtgaa ggattacttt cctgaacctg tgactgtctc atggaactct       540
ggtgctctga cttctggtgt ccacactttc cctgctgtgc tgcagtctag tggactgtac       600
tctctgtcat ctgtggtcac tgtgccctct tcatctctgg aacccagac  ctacatttgt       660 aatgtgaacc acaaaccatc caacactaaa gtggacaaaa agtggaacc  caaatcctgt       720 gacaaaaccc acacctgccc accttgtcct gccctgaac  tgctgggagg accttctgtg       780
tttctgttcc caccaaaacc aaaagatacc ctgatgatct ctagaacccc tgaggtgaca       840
tgtgtggtgg tggatgtgtc tcatgaggac cctgaggtca aattcaactg gtacgtggat       900
ggagtggaag tccacaatgc caaaaccaag cctagagagg aacagtacaa ttcaacctac       960
agagtggtca gtgtgctgac tgtgctgcat caggattggc tgaatggcaa ggaatacaag      1020
tgtaaagtct caaacaaggc cctgcctgct ccaattgaga aaacaatctc aaaggccaag      1080
ggacagccta gggaacccca ggtctacacc ctgccacctt caagagagga aatgaccaaa      1140
aaccaggtgt ccctgacatg cctggtcaaa ggcttctacc cttctgacat tgctgtggag      1200
tgggagtcaa atggacagcc tgagaacaac tacaaaacaa ccccccctgt gctggattct      1260
gatggctctt tctttctgta ctccaaactg actgtgaca  agtctagatg gcagcagggg      1320
aatgtctttt cttgctctgt catgcatgag gctctgcata accactacac tcagaaatcc      1380
ctgtctctgt ctcctggcaa aggcggcgga ggatccgggg gtgggggaag cggcggagga      1440
ggtagcgccg agacgtggga cacattggca tttgatggaa ggacatttgt tgagtacctc      1500
aatgcggtca cagaaagcga actcgccaac gaaatacctg tggagaaagc cctacagagt      1560
aatcacttcg agctgagttt aagaaccgag gctacacagg gcctagtgct ttggtccgga      1620
aaggccaccg agcgggctga ctatgtggcc ctggctatcg tggacggtca tctgcagctg      1680
tcgtataatt tgggcagcca accagtggtc ctcagatcta ctgtgcccgt caacacaaat      1740
cgctggctta gagttgttgc acatcgcgag caaagagagg gcagcttgca agtggggaat      1800
gaagcccctg tcaccggaag cagccctctc ggtgccactc agttggatac cgatggagcc      1860
ctgtggcttg gcggttttgcc agagttgcca gttggccctg ctctgcccaa ggcctatggg      1920
actggcttcg ttggatgcct tcgcgacgtg gtggtcggcc gtcacccct  tcaccttctc      1980 gaagatgcag tcaccaagcc agaattacgc ccttgtccaa ccccttgata agctt           2035
```

<210> SEQ ID NO 47
<211> LENGTH: 720
<212> TYPE: DNA
<213> ORGANISM: artificial sequence
<220> FEATURE:
<223> OTHER INFORMATION: expression vector

<400> SEQUENCE: 47

```
gcggccgcca tgaatttt gg actgaggctg atttttcctgg tgctgaccct gaaaggcgtc        60
cagtgtgaca tccaaatgac ccagtctcca tcctccctga gcgcgagtgt gggtgatcgc       120
gtgactataa cctgctccgc atcctcatca atctcgtaca tgcactggta tcagcagaag       180
cctggaaagg cacccaagct gcttatatac gataccctct aattggcaag aggggttccc       240
tccagattct ctgggagcgg gtctggtacc gactttactc taacgatctc atcactgcaa       300
ccggaagatt tcgccacata ctattgccag cagtggtacc tgcacccct  cacattcgga       360 ggtggcacga aagtggaaat caagcgtacg gtcgcggcgc ttctgtgtt  cattttcccc       420 ccatctgatg aacagctgaa atctggcact gcttctgtgg tctgtctgct gaacaacttc       480
```

```
taccctagag aggccaaagt ccagtggaaa gtggacaatg ctctgcagag tgggaattcc    540
caggaatctg tcactgagca ggactctaag gatagcacat actccctgtc ctctactctg    600
acactgagca aggctgatta cgagaaacac aaagtgtacg cctgtgaagt cacacatcag    660
gggctgtcta gtcctgtgac caaatccttc aataggggag agtgctgata gtaaaagctt    720

<210> SEQ ID NO 48
<211> LENGTH: 1443
<212> TYPE: DNA
<213> ORGANISM: artificial sequence
<220> FEATURE:
<223> OTHER INFORMATION: expression vector

<400> SEQUENCE: 48
gcggccgcca tgaattttgg actgaggctg attttcctgg tgctgacccT gaaaggcgtc     60
cagtgtcaat gcaattgca agagagcggg cccggactcg tgaaaccatc tgagaccctc    120
tccctcacct gcaccgtttc cggattctcc ctccggaaag tcggaagttc agtgtcctgg    180
atcagacagc ctcccggcaa gggcctggaa tggattggac acatctattg ggatgacgat    240
aagcgcctga tccctccct gcgcaatcgc gtgacaatca gcgtggatac cagcaagaat    300
caattctcac tgaaactttc tagcgtaaca gctgctgaca cggctgtata ttattgcgcc    360
cgccgcgcta ttactactgt catcggaggt gggacgttcg atctgtgggg acaggggact    420
ctggttactg tctcgagcgc tagcacaaag ggcctagtg tgtttcctct ggctccctct    480
tccaaatcca cttctggtgg cactgctgct ctgggatgcc tggtgaagga ttactttcct    540
gaacctgtga ctgtctcatg gaactctggt gctctgactt ctggtgtcca cactttccct    600
gctgtgctgc agtctagtgg actgtactct ctgtcatctg tggtcactgt gccctcttca    660
tctctgggaa cccagaccta catttgtaat gtgaaccaca aacatccaa cactaaagtg    720 gacaaaaaag tggaacccaa atcctgtgac aaaacccaca cctgcccacc ttgtcctgcc    780
cctgaactgc tgggaggacc ttctgtgttt ctgttccccc caaaaccaaa ggatacactg    840
atgatctcta gaaccctga ggtgacatgt gtggtggtgg atgtgtctca tgaggaccct    900
gaggtcaaat tcaactggta cgtggatgga gtggaagtcc acaatgccaa accaagcct    960 agagaggaac agtacaattc aacctacaga gtggtcagtg tgctgactgt gctgcatcag   1020
gattggctga atggcaagga atacaagtgt aaagtctcaa acaaggccct gcctgctcca   1080
attgagaaaa caatctcaaa ggccaaggga cagcctaggg aaccccaggt ctacaccctg   1140
ccaccttcaa gagaggaaat gaccaaaac caggtgtccc tgacatgcct ggtcaaaggc   1200
ttctacccct tgacattgc tgtggagtgg gagtcaaatg gacagcctga gaacaactac   1260
aaaacaaccc cccctgtgct ggattctgat ggctcttctct ttctgtactc caaactgact   1320
gtggacaagt ctagatggca gcaggggaat gtcttttctt gctctgtcat gcatgaggct   1380
ctgcataacc actacactca gaaatccctg tctctgtctc ccgggaaatg atagtaaaag   1440
ctt                                                                 1443

<210> SEQ ID NO 49
<211> LENGTH: 2062
<212> TYPE: DNA
<213> ORGANISM: artificial sequence
<220> FEATURE:
<223> OTHER INFORMATION: expression vector

<400> SEQUENCE: 49
```

```
gcggccgcca tgaattttgg actgaggctg attttcctgg tgctgaccct gaaaggcgtc    60
cagtgtcaat tgcaattgca agagagcggg cccggactcg tgaaccatc  tgagaccctc   120
tccctcacct gcaccgtttc cggattctcc ctccggaaag tcggaagttc agtgtcctgg   180
atcagacagc ctcccggcaa gggcctggaa tggattggac acatctattg ggatgacgat   240
aagcgcctga atccctccct cgcaatcgc  gtgacaatca gcgtggatac cagcaagaat   300
caattctcac tgaaactttc tagcgtaaca gctgctgaca cggctgtata ttattgcgcc   360
cgccgcgcta ttactactgt catcggaggt gggacgttcg atctgtgggg acaggggact   420
ctggttactg tctcgagcgc tagcacaaag ggccctagtg tgtttcctct ggctccctct   480
tccaaatcca cttctggtgg cactgctgct ctgggatgcc tggtgaagga ttactttcct   540
gaacctgtga ctgtctcatg gaactctggt gctctgactt ctggtgtcca cactttccct   600
gctgtgctgc agtctagtgg actgtactct ctgtcatctg tggtcactgt gccctcttca   660
tctctgggaa cccagaccta catttgtaat gtgaaccaca aaccatccaa cactaaagtg   720
gacaaaaaag tggaacccaa atcctgtgac aaaacccaca cctgcccacc ttgtcctgcc   780
cctgaactgc tgggaggacc ttctgtgttt ctgttcccac caaaaccaaa agataccctg   840
atgatctcta gaacccctga ggtgacatgt gtggtggtgg atgtgtctca tgaggaccct   900
gaggtcaaat tcaactggta cgtggatgga gtggaagtcc acaatgccaa accaagcct   960
agagaggaac agtacaattc aacctacaga gtggtcagtg tgctgactgt gctgcatcag  1020
gattggctga atggcaagga atacaagtgt aaagtctcaa acaaggccct gcctgctcca  1080
attgagaaaa caatctcaaa ggccaaggga cagcctaggg aacccaggt  ctacaccctg  1140
ccaccttcaa gagaggaaat gaccaaaaac caggtgtccc tgacatgcct ggtcaaaggc  1200
ttctacccct tctgacattg ctgtggagtg gagtcaaatg gacagcctga gaacaactac  1260
aaaacaaccc ccctgtgct  ggattctgat ggctctttct ttctgtactc caaactgact  1320
gtggacaagt ctagatggca gcaggggaat gtcttttctt gctctgtcat gcatgaggct  1380
ctgcataacc actacactca gaaatccctg tctctgtctc ctggcaaagg cggcggagga  1440
tccgggggtg ggggaagcgg cggaggaggt agcgccggag acgtggacac attggcattt  1500
gatggaagga catttgttga gtacctcaat gcggtcacag aaagcgaact cgccaacgaa  1560
ataccgtgg  agaaagccct acagagtaat cacttcgagc tgagtttaag aaccgaggct  1620
acacagggcc tagtgctttg gtccggaaag gccaccgagc gggctgacta tgtggccctg  1680
gctatcgtgg acggtcatct gcagctgtcg tataatttgg gcagccaacc agtggtcctc  1740
agatctactg tgcccgtcaa cacaaatcgc tggcttagag ttgttgcaca tcgcgagcaa  1800
agagagggca gcttgcaagt ggggaatgaa gcccctgtca ccggaagcag ccctctcggt  1860
gccactcagt tggataccga tggagccctg tggcttggcg gtttgccaga gttgccagtt  1920
ggccctgctc tgcccaaggc ctatgggact ggcttcgttg gatgccttcg cgacgtggtg  1980
gtcggccgtc accccttca  ccttctcgaa gatgcagtca ccaagccaga attacgccct  2040
tgtccaaccc cttgataagc tt                                           2062
```

<210> SEQ ID NO 50
<211> LENGTH: 1671
<212> TYPE: DNA
<213> ORGANISM: artificial sequence
<220> FEATURE:
<223> OTHER INFORMATION: expression vector

<400> SEQUENCE: 50

```
gcggccgcca tgaattttgg actgaggctg attttcctgg tgctgaccct gaaaggcgtc    60
cagtgtggta actgttggct gcggcaggct aaaaatggta gatgtcaggt gctgtataaa   120
accgaactgt caaaagaaga gtgttgctcc acaggaaggc tgtctaccag ttggacagag   180
gaagacgtga acgataatac tctgttcaag tggatgatct ttaacggcgg cgccsctaat   240
tgcattccct gtaaagagac ctgcgaaaac gtggattgtg gacctgggaa gaaatgcaga   300
atgaacaaga aaaataagcc tcgctgcgtg tgtgcacccg attgcagcaa catcacctgg   360
aagggcccag tctgtggact ggacgggaaa acatacagga tgagtgcgc actgctgaag   420 gcccggtgta agaacagcc agagctgaa gtgcagtatc agggcaagtg caagaaaact   480
tgtagagacg tcttctgccc cggctcctct acttgtgtgg tcgatcagac caacaatgcc   540
tactgcgtga cttgtaaccg catctgcccc gagccttcta gttcagaaca gtacctgtgt   600
ggtaatgatg gcgtcacata ttccagcgct tgccacctgc gaaaggcaac ttgtctgctg   660
ggacgttcca ttgggctggc ctatgagggc aaatgcatca aggctaaatc ctgcgaagac   720
attcagtgtg ggggtggcaa gaaatgtctg tgggatagta agtgggtag gggccggtgc   780 tctctgtgtg acgaactgtg ccccgactca aaatccgatg aacctgtctg tgcaagcgac   840
aatgccacct acgcttctga gtgtgccatg aaggaagctg cctgctcaag cggcgtgctg   900
ctggaagtca acatagcgg tagttgtaat ggcggtggag gatccggtgg aggcggttct   960
ggcggcggtg gtagtgacaa acccacacc tgcccacctt gtcctgcccc tgaactgctg  1020
ggaggacctt ctgtgtttct gttcccacca aaaccaaaag atacccgtat gatctctaga  1080 accctgagg tgacatgtgt ggtggtggat gtgtctcatg aggaccctga ggtcaaattc  1140
aactggtacg tggatggagt ggaagtccac aatgccaaaa ccaagccag agaggaacag  1200 tacaattcaa cctacagagt ggtcagtgtg ctgactgtgc tgcatcagga ttggctgaat  1260
ggcaaggaat acaagtgtaa agtctccaaac aaggccctgc ctgctccaat tgagaaaaca  1320
atctcaaagg ccaagggaca gcctagggaa cccagggtct acaccctgcc accttcaaga  1380
gaggaaatga ccaaaaacca ggtgtccctg acatgctgg tcaaaggctt ctacctttct  1440
gacattgctg tggagtggga gtcaaatgga cagcctgaga caactacaa acaacccac  1500 cctgtgctgg attctgatgg ctcttctttct ctgtactcca aactgactgt ggacaagtct  1560
agatggcagc aggggaatgt cttttcttgc tctgtcatgc atgaggctct gcataaccac  1620
tacactcaga atccctgtc tctgtctcct ggcaaatgat agtaaaagct t             1671
```

<210> SEQ ID NO 51
<211> LENGTH: 2290
<212> TYPE: DNA
<213> ORGANISM: artificial sequence
<220> FEATURE:
<223> OTHER INFORMATION: expression vector

<400> SEQUENCE: 51

```
gcggccgcca tgaattttgg actgaggctg attttcctgg tgctgaccct gaaaggcgtc    60
cagtgtggta actgttggct gcggcaggct aaaaatggta gatgtcaggt gctgtataaa   120
accgaactgt caaaagaaga gtgttgctcc acaggaaggc tgtctaccag ttggacagag   180
gaagacgtga acgataatac tctgttcaag tggatgatct ttaacggcgg cgccsctaat   240
tgcattccct gtaaagagac ctgcgaaaac gtggattgtg gacctgggaa gaaatgcaga   300
atgaacaaga aaaataagcc tcgctgcgtg tgtgcacccg attgcagcaa catcacctgg   360
```

-continued

| | |
|---|---|
| aagggcccag tctgtggact ggacgggaaa acatacagga atgagtgcgc actgctgaag | 420 |
| gcccggtgta aagaacagcc agagctggaa gtgcagtatc agggcaagtg caagaaaact | 480 |
| tgtagagacg tcttctgccc cggctcctct acttgtgtgg tcgatcagac caacaatgcc | 540 |
| tactgcgtga cttgtaaccg catctgcccc gagccttcta gttcagaaca gtacctgtgt | 600 |
| ggtaatgatg gcgtcacata ttccagcgct tgccacctgc gaaaggcaac ttgtctgctg | 660 |
| ggacgttcca ttgggctggc ctatgagggc aaatgcatca aggctaaatc ctgcgaagac | 720 |
| attcagtgtg ggggtggcaa gaaatgtctg tgggatagta agtgggtag gggccggtgc | 780 |
| tctctgtgtg acgaactgtg ccccgactca aaatccgatg aacctgtctg tgcaagcgac | 840 |
| aatgccacct acgcttctga gtgtgccatg aaggaagctg cctgctcaag cggcgtgctg | 900 |
| ctggaagtca acatagcgg tagttgtaat ggcggtggag gatccggtgg aggcggttct | 960 |
| ggcggcggtg gtagtgacaa aacccacacc tgcccacctt gtcctgcccc tgaactgctg | 1020 |
| ggaggacctt ctgtgtttct gttcccacca aaaccaaaag ataccctgat gatctctaga | 1080 |
| acccctgagg tgacatgtgt ggtggtggat gtgtctcatg aggaccctga ggtcaaattc | 1140 |
| aactggtacg tggatggagt ggaagtccac aatgccaaaa ccaagcctag agaggaacag | 1200 |
| tacaattcaa cctacagagt ggtcagtgtg ctgactgtgc tgcatcagga ttggctgaat | 1260 |
| ggcaaggaat acaagtgtaa agtctcaaac aaggccctgc ctgctccaat tgagaaaaca | 1320 |
| atctcaaagg ccaagggaca gcctagggaa ccccaggtct acaccctgcc accttcaaga | 1380 |
| gaggaaatga ccaaaaacca ggtgtccctg acatgcctgg tcaaaggctt ctacccttct | 1440 |
| gacattgctg tggagtggga gtcaaatgga cagcctgaga caactacaa acaaccccc | 1500 |
| cctgtgctgg attctgatgg ctcttttcttt ctgtactcca aactgactgt ggacaagtct | 1560 |
| agatggcagc aggggaatgt cttttcttgc tctgtcatgc atgaggctct gcataaccac | 1620 |
| tacactcaga atccctgtc tctgtctcct ggcaaaggcg gcggaggatc cggggggtggg | 1680 |
| ggaagcggcg gaggaggtag tgtgggagac ctggagaccc tggcttttga cgggcggaca | 1740 |
| tacattgaat acctgaacgc tgtgaccgag agtgaactga ctaatgagat ccctgcagaa | 1800 |
| aagggccctgc agtcaaacca cttcgagctg tccctgagga ccgaagcaac acagggactg | 1860 |
| gtcctgtgga tcggcaaagt gggagagcga gcagactaca tggccctggc tattgtggat | 1920 |
| ggccatctgc agctgtctta tgacctggga agtcagccag tggtcctgag gtctacagtc | 1980 |
| aaagtgaaca ctaatagatg gctgagggtg cgggctcaca gagagcatcg cgaagggagc | 2040 |
| ctgcaggtcg gtaatgaagc accagtgacc ggctccagcc ctctgggagc aactcagctg | 2100 |
| gacaccgatg gggctctgtg gctgggagga ctgcagaagc tgccagtcgg ccaggctctg | 2160 |
| cccaaagcat acgggacagg ttttgtgggg tgcctgcgag atgtggtcgt gggtcaccgt | 2220 |
| cagctgcacc tgctggagga cgctgtcact aagcctgaac tgagaccttg ccctacccctg | 2280 |
| tgataagctt | 2290 |

MUSCLE PERFORMANCE IMPROVEMENT COMPOUNDS COMPRISING C-TERMINUS AGRIN FRAGMENT AND AN ACTR2B INHIBITOR

CROSS REFERENCE TO RELATED APPLICATIONS

This application is a national stage application of International Application No. PCT/IB2017/057436, filed 28 Nov. 2017, which claims priority from Great Britain Patent Application No. 1620119.6, filed 29 Nov. 2016, which applications are incorporated herein by reference.

This disclosure relates to a method of treating pathological disorders or diseases affecting the function of muscles and to compounds for use in such treatments. The methods are particularly suitable for treating, preventing, ameliorating or diagnosing pathological disorders.

Muscles are the contractile tissue responsible for all movement in living organisms. Any loss of muscle function is invariably harmful to a greater or lesser extent. Key elements of muscle function are strength, power and endurance, Muscle strength is the amount of force a muscle, or group of muscles, can exert upon maximal contraction, generally against an external load. Muscle strength is expressed as the greatest measurable force that can be exerted by a muscle or muscle group to overcome resistance during a single, maximal effort. Muscle power is force developed quickly and combines strength and speed. It is the rate of performing work. Muscular endurance is the ability of a muscle or group of muscles to sustain in a prolonged fashion or repeatedly exert force against resistance.

These performances can be evaluated by regular assessments of a subject in a testing regime, such as an exercise machine. Most important is the loss of muscle endurance. For example, improvement in a 6-minute walking test or "6MWT" (see, for example, Bautmans et al (BMC Geriatr. 2004 Jul. 23;4:6)) and Enright (Respir Care. 2003 August; 48(8):783-5) is a prerequisite for approval by regulatory authorities such as the US Food and Drug Administration of a drug intended to treat pathological disorders affecting the functioning of the muscle.

There are many pathological disorders that can lead to the loss of muscle function. As used herein, a "pathological disorder" includes, but is not limited to, neuromuscular diseases. Neuromuscular diseases is a very broad term that encompasses many diseases and ailments that impair the functioning of the muscles, either directly, being pathologies of the voluntary muscle, or indirectly, being pathologies of nerves or neuromuscular junctions.

One pathological disorder that can lead to loss of muscle function is muscle atrophy. There are many causes of muscle atrophy, including the result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barre syndrome, peripheral neuropathy, or exposure to environmental toxins or drugs).

In addition, the muscle atrophy can be a result of myopathy, such as myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomositisis; polymyositis; inclusion body myositis; myositis ossificans; rhabdomyolysis and myoglobinurias.

The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. The musculoskeletal disease can also be osteoporosis, a bone fracture, short stature, or dwarfism.

Other pathological disorders that can lead to the loss of muscle function are adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, renal failure, congestive heart failure, ageing, space travel or time spent in a zero gravity environment, Examples of age-related conditions that may be treated include, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, frailty, memory loss, wrinkles, impaired kidney function, and age-related hearing loss; metabolic disorders, including Type II Diabetes, Metabolic Syndrome, hyperglycemia, and obesity. Of course, patients may simultaneously suffer from one or more of these conditions, for example, sarcopenia and pulmonary emphysema, or sarcopenia and impaired kidney function, Other conditions that are considered to be "pathological disorders" as recited herein include acute and/or chronic renal disease or failure, liver fibrosis or cirrhosis, cancer such as breast cancer, Parkinson's Disease; conditions associated with neuronal death, such as ALS, brain atrophy, or dementia and anemia. In addition, there are losses suffered as a consequence of age, trauma or inactivity.

Further conditions include cachexia, cachexia associated with a rheumatoid arthritis and cachexia associated with cancer.

To date, very few reliable or effective therapies have been developed to treat these disorders Individual aspects of muscular problems have been addressed. For example, one potential avenue of treatment for loss of muscle mass is the inhibition of myostatin. Myostatin, sometimes referred to as GDF-8 (growth differentiation factor-8), is one of a family of dimeric growth and differentiation factors which belong to the transforming growth factor-beta (TGF-beta) superfamily of structurally related signaling proteins. These proteins signal through a heterodimeric complex of receptor serine kinases which include at least two type I receptors, ActRIB (ALK4) and ActRIC (ALK7) and two type II receptors, ActRIIA (ACVR2A) and ActR2B (ACVR2B). These receptors are all transmembrane proteins, composed of a ligand-binding extracellular domain with cysteine-rich region, a transmembrane domain, and a cytoplasmic domain with predicted serineithreonine specificity. Type I receptors are essential for signaling while type II receptors are required for binding ligands and for expression of type I receptors. Type I and II receptors form a stable complex after ligand binding resulting in the phosphorylation of type I receptors by type II receptors.

The activity receptor II B (ActR2B) is a receptor for myostatin (GDF8) but numerous other members of the TGF-beta super family, such as Activin B, Activin AB, Inhibin A, Inhibin B, GDF3, GDF11, Nodal, BMP2, BMP4, BMP7, BMP9, and BMP10 bind to and activate ActR2B as well (see, for example Tsuchida et al (Endocrine journal 2008 55(1), 11-21). Blocking the interactions of ActR2B with its ligands can lead to beneficial physiological effects. The interaction between myostatin and this receptor regulates the inhibition of skeletal muscle differentiation via the Smad-dependent pathway, (SMADs are intracellular proteins that transduce extracellular signals from transforming growth factor beta ligands, like myostatin to the nucleus where they activate downstream gene transcription). Thus, by inhibiting or preventing myostatin from binding to ActR2B, one can induce the formation of skeletal muscle.

Various groups have looked into this. Bogdanovich et al (Nature, 2002, 420:418-421) describes that anti-myostatin antibodies were able to block myostatin, resulting in an increase in muscle mass in a mouse model of Duchenne muscular dystrophy. Bradley et al (Cell Mol. Life. Sci, 2008, 65:2119-2124) have reviewed the different available approaches for modulating the myostatin/ActR2B interaction, including the aforementioned anti-myostatin antibodies, inhibiting the release of mature myostatin by administering the myostatin propeptide, administering follistatin to block the myostatin receptor, administering HDAC inhibitors to induce follistatin production, administering an altered myostatin peptide which prevents myostatin from binding the receptor and administering a soluble decoy receptor for myostatin.

Myostatin acts to inhibit muscle fibre growth and muscle stem cell growth. Studies have shown that animals either lacking myostatin or treated with substances that block the activity of myostatin have significantly larger muscle mass. Furthermore, individuals who have mutations in both copies of the myostatin gene have significantly increased muscle mass and in many cases are stronger than normal. In a particular case, described in N Engl J Med 2004; 350:2682-2688 (Jun. 24, 2004), a baby born with unusually muscular development turned out to have a deficiency of myostatin, believed due to a defect in the gene responsible for its production.

A number of recent publications have sought to exploit this as a treatment, for example:

Myostatin binding proteins such as ActR2B polypeptides (e.g. U.S. Pat. Nos. 7,842,663 and 8,614,292),
follistatin (e.g. U.S. Pat. No. 6,004,937)
anti-ActR2B antibodies (e.g. U.S. Pat. No. 8,551,482)
anti-myostatin antibodies (e.g. U.S. Pat. Nos. 7,261,893, 8,063,188, 8,415,159, 8,551,482 and 8,710,212)
anti-activin antibodies (e.g. US 20150037339 A1, WO 2009137075 A1)

Muscular hypertrophy and/or atrophy is not the whole story. Another factor is denervation. Muscle contraction is triggered by impulse from the nerves through release of electrical and chemical messages. Nerves also provide the muscle fibers with a number of trophic factors, essential to the well-being and proper functioning of the muscle. The connection between nerves and muscle occurs via a highly complex synaptic structure called the neuromuscular junction (NMJ). Loss of NMJs results in the reduction of muscular function, independently of the anatomical and biochemical integrity of the muscle itself.

Some approaches have focussed on preventing loss of neuro-muscular junctions. For correct maintenance of NMJs, it has been shown by, for example, Wu et al (Development. 2010 April:137(7)1017-33. doi; 10.1242/dev, 038711) and Tezuka et al (Proc Natl Acad Sci USA, 2014. Nov. 18;111(46):16556-61) that agrin is important for their formation and maintenance of a neuromuscular junction.

It has nevertheless been found that even the combination of increased muscle mass and treatment seeking to retain NMJs does not prevent the loss of muscle performance (measured by the performance of suitably treated mice on a treadmill). In short, while there are a number of methods for improving individual aspects of muscle problems, there currently exists nothing that can counteract the overall loss of muscle performance.

It has now been found that a particular group of linked proteins, polypeptides and monoclonal antibodies has given exceptional results in improving muscle performance.

Therefore, there is provided a compound comprising at least two components, a first component being the nLG3 or (h)nLG3 domain from the C-terminus of mouse or human agrin, and at least one second component, selected from proteins or an antagonistic antibody that inhibit ActR2B-induced signaling activity in the presence of myostatin, the components being linked by means of linking entities.

There is additionally provided a method of improving muscle performance, comprising the administration of an effective amount of a compound as hereinabove defined.

By "improving muscle performance" is meant that muscular endurance especially is improved. It is a surprising fact that, although the compounds hereinabove defined do not provide much more muscle mass (myostatin) nor do they cluster acetyl choline receptors efficiently (at least 100-1000 times lower than a fully active agrin fragment), the overall muscular performance as measured by the endurance is remarkably improved. This can be demonstrated by the experimental methods hereinafter described.

With respect to amino acid sequences suitable for use in, and described in, this disclosure, the sequences should be at least 75% identical to those set forth hereinunder. More particularly, they may be 80%, 85%, 90% or 95% identical, most particularly 95% identical. In the case of inserts in the agrin (described in detail hereinunder), the inserts should be at least 95% identical. In a particular embodiment, all amino acid sequences are at least 95% identical.

The first component is the nLG3 domain from the C-terminus of agrin. Agrin is a large heparan proteoglycans with a molecular weight of 400-600 kDa, (Database accession number NP-940978). The protein core consists of about 2000 amino acids and its mass is about 225 kDa. It is a multidomain protein composed of 9 K (kunitz-type) domains, 2 LE (laminin-EGF-like) domains, one SEA (sperm protein, enterokinase and agrin) domain, 4 EG (epidermal growth factor-like) domains and 3 LG (laminin globular) domains. Agrin is a very important protein and agrin-deficient mice die at birth due to respiratory failure. This is caused by the fact that agrin is strictly required for the proper innervation of muscle fibers and that these mice are not able to build proper NMJs.

Agrin exists in several splice variants and can be expressed as a secreted protein, containing the N-terminal NIA (N-terminal agrin) domain, which is the most abundant form of agrin and the predominant form expressed in motor neurons. It is produced in the soma of the neurons, transported down the axon and released from the axon ending of the motor nerve into the synaptic cleft of the NMJ. Here it acts as an agonist of LRP4 and may also become a component of the basal lamina. In the CNS, most agrin is expressed as a type-II transmembrane protein by alternative splicing at the N-terminus lacking the N-terminal NtA domain (Bezakova and Ruegg, 2003).

The serine/threonine (S/T) rich segments in agrin are responsible for a high degree of glycosylation, containing several glycosylation and glucosaminoglycan attachment sites giving rise to the big mass of the proteoglucan. The C-terminal, 75 kDa moiety of agrin starting with the first EG domain, is required for full activity in acetylcholine receptor (AChR) clustering activity on muscle cells, although the most C-terminal 20 kDa fragment is sufficient to induce AChR aggregation (Bezakova and Ruegg, 2003). Several binding sites for interaction partners of agrin, including α-dystroglycan, heparin, some integrins and LRP4, are mapped to the C-terminal region. The large heparansulfate side chains are binding sites for heparin binding proteins, e.g. some growth factors.

In the C-terminal part of human agrin, there are 2 alternative splice sites y and z At the y-site, there may be inserts of 0, 4, 17 or 21 (4+17) amino acids and at the z site there may be inserts of 0, 8, 11 or 19 (8+11) amino acids. The function of the four inserted amino acids in the y-site is to create a heparin binding site. Motor neurons express predominantly y4 agrin. The most important splice site of agrin in respect of NMJ maturation is the z-site, giving agrin the ability to be active as an acetylcholine-receptor clustering agent. It is well known that full-length agrin containing the insertion of 8 amino acids at the z-site in presence of the 4-amino acid insert in splice site y (y4z8) generates an agrin variant with a half maximal AChR clustering activity of 35 pM in cultured myotube clustering assays. The insertion of 11 amino acids gives rise to a half-maximal AChR clustering activity while the 19 amino acid insertion results in a half-maximal AChR clustering activity of 110 pM. Agrin without an insertion at this site is not active in clustering acetylcholine-receptors on the in-vitro cultured myotubes (Bezakova and Ruegg, 2003). Thus, the most active form of agrin in the clustering assay is the y4z8 variant, which is expressed by motor neurons.

A 40 kDa C-terminal fragment of agrin (y4z8) containing the LG2, EG4 and the LG3 domains was found to be active in AChR clustering with an EC50 of 130 pM in the AchR clustering activity while shorter fragments have only lower activities. The C-terminal LG3 domain with the z8 insertion, the so-called LG3z8 domain, exhibits a half maximal AChR clustering activity of only 13 nM, which is a factor 100 fold lower than the 40 kDa fragment (Bezakova and Ruegg, 2003).

During the development and maturation of the NMJ, agrin is a key player of molecules involved in the clustering of acetycholine receptors. While NMJs are destabilized by the neurotransmitter acetyl choline, agrin, which is secreted by the motor neuron, stabilizes and increases the clusters of the AChR's via phosphorylation of MuSK, a membrane bound receptor tyrosine kinase. The interaction of agrin with MuSK is postulated to be mediated via LRP4, a low-density lipoprotein receptor (LDLR)-related protein. It was found that agrin (y4z8) has a 10-fold higher affinity to LRP4 than agrin (y4z0) giving rise to the differential AChR clustering activity of the different agrin splice variants observed in the in vitro cultured myotube assays. Upon agrin binding, LRP4 causes self-phosphorylation of MuSK, which then activates the signal cascade for the expression and clustering of acetylcholine receptors. It has been shown that a 44-kD fragment of agrin leads to the formation of clusters of acetyl choline receptors on the surface of muscle cells (see Hettwer et al (PLOS ONE February 2014. Vol. 9, Issue 2, e88739)), which is believed to be the initial step in the formation of a NMJ.

The term "LG3" as used in this disclosure means the mouse-derived 22 kDa C-terminal agrin fragment of SEQ ID NO: 1 (all sequences are appended to this disclosure and form part thereof). The term "nLG3" as used in this disclosure means the LG3 fragment which further contains an insertion of 8, 11 or 19 amino acids at the z-site. The inserted sequences at the z-site are ELTNEIPA (z8, SEQ ID NO: 2), PETLDSRALFS (z11, SEQ ID NO: 3) or ELTNEIPA-PETLDSRALFS (z19, SEQ ID NO: 4, a combination of SEQ ID NO: 2 and SEQ ID NO: 3). An example of nLG3 is SEQ ID NO: 5

The term "(h)LG3" as used in this disclosure means the human derived 22 kDa C-terminal agrin fragment of SEQ ID NO: 6. The term "(h)nLG3" as used in this disclosure means the (h)LG3 fragment which further contains an insertion of 8, 11 or 19 amino acids at the z-site. The inserted sequences at the z-site ELANEIPV (z8, SEQ ID NO: 7), PETLDSGALHS (z11, SEQ ID NO: 8) or ELANEIPV-PETLDSGALHS (z19, SEQ ID NO: 9, a combination of SEQ ID NO: 7 and SEQ ID NO: 9). A particular example of (h)nLG3 is SEQ ID NO: 10 nLG3 may include additional amino acids at the N-terminus or C-terminus. Such additional amino acids at the N-terminus are e.g. present due to the method of preparation by recombinant synthesis and expression in suitable cells.

Proteins containing elongations at the N-terminus by one or more domains of agrin up to the natural N-terminus of agrin are also included, as well as glycosylated or in other ways post-translationally, enzymatically or chemically modified protein variants of human agrin.

The second component is selected from proteins or antagonistic antibodies that inhibit ActR2B-mediated signaling activity in the presence of myostatin. Examples of a second component as used herein refers to a protein or an antagonistic antibody such as actR2B (AcvRIIB, actRIIB), or acvRA (actR2, actRII), alk4, alk5. The term ActR refers to soluble extracellular part of the mouse ActR2B receptor as defined in SEQ ID NO: 11, This extracellular part is any part of the transmembrane protein that projects into the environment surrounding a cell. The term (h)ActR refers to extracellular part of the human ActR2B receptor as defined in SEQ ID NO: 12 (AAC64515.1, GI:3769443), Another example is follistatin as defined in SEQ ID NO: 25.

An example of a monoclonal antibody (mAb) that inhibits ActR2B-mediated signaling activity is ActRmAb (U.S. Pat. No. 8,551,482). Antibodies consist of a light chain (LC) and a heavy chain (HC). A typical example of the LC of ActRmAb (ActRmAb(LC)) is as defined in SEQ ID NO: 29. The HC of ActRmAb (ActRmAb(HC)) is as defined in SEQ ID NO: 28. The (h)nLG3 connected to ActRmAb(HC) (ActRmAb(HC)-(h)nLG3) is defined in SEQ ID NO: 30 Another example of an antibody is MyomAb (U.S. Pat. No. 8,063,188). This antibody is directed against myostatin and prevents binding of myostatin to the (h)ActR receptor. A typical example of the LC of MyomAb (MyomAb(LC)) is as defined in SEQ ID NO: 32, The HC of MyomAb (MyomAb (HC)) is as defined in SEQ ID NO: 31. The (h)nLG3 connected to MyomAb(HC) (MyomAb(HC)-(h)nLG3) is defined in SEQ ID NO: 33.

This ActR2B-mediated signal-inhibiting activity of mAbs may be readily ascertained by means of an assay, Such an assay can include, for example, a Smad-dependent reporter gene assay, inhibition of myostatin-induced Smad phosphorylation (P-Smad ELISA) and inhibition of myostatin-induced inhibition of skeletal muscle cell differentiation (for instance by a creatine kinase assay).

In some embodiments, the second component inhibits myostatin-induced signaling as measured in a Smad-dependent reporter gene assay at an IC50 of 10 nM or less, 1 nM or less, or 100 pM or less.

In some instances, it is possible for a compound according to this disclosure to comprise an additional component, meaning that there will be three components, joined by two linking entities. The third component acts as a stabiliser component, that is, it increases in vivo serum half-life. This may be as a result of decreased destruction, decreased clearance by the kidney, or other pharmacokinetic effect. "In vivo serum half-life" refers to the half-life of a protein circulating in the blood of an organism. Fusions with the Fc region of an immunoglobulin (IgG molecule) are known to confer desirable pharmacokinetic properties and increase serum half-life on a wide range of proteins. The term "Fc region of an IgG molecule" refers to the Fc domain of an immunoglobulin of the isotype IgG, as is well known to those skilled in the art. The Fc region of an IgG molecule is that portion of IgG molecule (IgG1, IgG2, IgG3, and IgG4) that is responsible for increasing the in vivo serum half-life of the IgG molecule.

The third component may also be selected so as to confer a desired property. For example, some domains are particularly useful for isolation of the resulting proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress.™. system (Qiagen) useful with (HIS.sub.6) fusion partners. As another example, the third domain may be selected so as to facilitate detection of the ActR2B polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the third domain might have a protease cleavage site, such as for Factor Xa or Thrombin, which allows the relevant protease to partially digest the fusion proteins and thereby liberate the recombinant proteins therefrom. The liberated proteins can then be isolated from the third domain by subsequent chromatographic separation. In certain preferred embodiments, the ActR domain and the (h)nLG3 domain are linked to a domain that stabilizes the resulting polypeptide in vivo.

A typical example of a third component is an "Fc" domain SEQ ID NO: 14.

Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

A linking entity is a short stretch of amino acids, linking two protein components. This unstructured linker may correspond to the roughly 15 amino acid unstructured region at the C-terminal end of the extracellular domain of ActR2B (the "tail"), or it may be an artificial sequence of between 5 and 15, 20, 30, 50 or more amino acids that are relatively free of secondary structure. A linker may be rich in glycine and proline residues and may, for example, contain repeating sequences of threonine/serine and glycines. Often multiple repeats of the sequence gggs are used (Glycin-Glycin-Glycin-Serin). Glycin gives flexibility and Serin is polar. A linking may be rich in glycine and proline residues and may, for example, contain repeating sequences of threonine/serine and glycines (e.g., TG.sub.4 or SG.sub.4 repeats).A typical linker sequence "L" is as defined in SEQ ID NO: 13. A fusion protein may include a purification subsequence, such as an epitope tag, a FLAG tag, a polyhistidine sequence, and a GST fusion.

Examples of ActR domain containing protein linked to a Fc domain are ActR-Fc (SEQ ID NO: 19), Fc-ActR (SEQ ID NO: 20) and (h)ActR-Fc (SEQ ID NO: 21). (Cadena et al. J Appl Physiol 109: 635-642. 2010). Example of a follistatin linked to an Fc domain is defined in SEQ ID NO: 26.

Examples of nLG3 domain-containing protein linked to a Fc domain are nLG3-Fc (SEQ ID NO: 16), Fc-nLG3 (SEQ ID NO: 15) and Fc-(h)nLG3 (SEQ ID NO: 17). An example of a LG3 domain without insert Fc-(h)LG3 (SEQ ID NO: 18) was also constructed Particular embodiments include the following components A-LB
B-L-A
A-L-C-L-B
B-L-C-L-A
C-L-B-L-A
C-L-A-L-B
B-L-A-L-C
A-L-B-L-C
A-L-D
D-L-A
A-L-E
E-L-A in which A represents an agrin nLG3 domain-containing protein, B represents an extracellular domain of the ActRIB, ActRIC, ActRIIA, ActR2B receptor protein and follistatin C represents a "stabiliser" domain, D represents ActR2B-mediated signal-inhibiting mAb against the ActRIB, ActRIC, ActRIIA, and ActR2B receptor protein, E represents ActR2B-mediated signal-inhibiting mAb against a member of the TGF-beta super family L represents a linking entity.

particular combinations being B-L-C-L-A, D-L-A and E-L-A

Examples of these particular combinations are ActR-Fc-nLG3 as defined in SEQ ID NO: 22, (h)ActR-Fc-(h)nLG3 as defined in SEQ ID NO: 23, Fol-Fc-nLG3 as defined in SEQ ID NO: 27. The ActRmAb(HC) linked to (h)nLG3 (ActRmAb(HC)-(h)nLG3) as defined in SEQ ID NO: 30. The MyomAb(HC linked to (h)nLG3) (MyomAb(HC)-(h)nLG3) as defined in SEQ ID NO: 33. The corresponding light chains of the antibodies need to be co-expressed with the heavy chains to create a fully functional antibody.

The heavy and light chains of the antibodies according to this disclosure may be expressed as contiguous single-chain proteins, with the first and second components joined by the linking entity (see e.g. Bird et alp 1988 Science 242:423-426; Huston et al., 1988 Proc. Natl. Acad. Sci. USA 85:5879-5883; McCafferty et al., 1990 Nature 348:552-554). The contiguous single chain protein can be linked to (h)nLG3.

The compounds of this disclosure may be made by known methods. For example, the DNA coding for the compound is expressed in suitable expression systems and the resulting protein is subsequently purified. Several prokaryotic and eukaryotic expression systems are suitable for the production and secretion of the compounds of the disclosure. Prokaryotic expression systems include, but are not limited to, expression in *E. coli*. Eukaryotic expression systems include expression in mouse myeloma cells, baculovirus-mediated expression in insect cells, as well as expression in human embryonic kidney (HEK) cells, transient expression in Chinese hamster ovary (CHO) cells and stable expression in Pichia pastoris. These systems have the advantage that they can easily be adapted to serum-free conditions to reduce the amount of contaminating proteins in the supernatant and can be adapted for large scale production. In addition, a variety of cell lines may be used, including HEK293T and HEK293-cells, COS cells, CHO cells, HeLa cells, H9 cells, Jurkat cells, NIH3T3 cells, C127 cells, CV1 cells, CAP cells or SF cells.

The sequence of a component may be adjusted, as appropriate, depending on the type of expression system used, as mammalian, yeast, insect and plant cells may all introduce differing glycosylation patterns that can be affected by the amino acid sequence of the peptide. In general, proteins for use in humans will be expressed in a mammalian cell line that provides proper glycosylation, such as HEK293 or CHO cell lines, although other mammalian expression cell lines are also expected to be useful.

The compounds of the disclosure may be purified by standard protein purification technologies. Immunoglobulins G may be purified using protein A or G. His-tagged protein can be purified using IMAC, but ion exchange chromatography or affinity purification using a heparin column can be used as well. Purification via an antibody raised against the C-terminal part of agrin can also be used. The eluted protein can then further be purified using a hydroxyapatite column or by gel filtration.

The compounds of this disclosure are useful in pharmaceutical compositions. The disclosure therefore provides a pharmaceutical composition comprising at least one compound as hereinabove described, formulated together with a pharmaceutically-acceptable carrier.

The pharmaceutical compositions of this disclosure are particularly useful for the treatment of pathological conditions leading to the loss of muscle function. Non-limiting examples of such conditions include:

muscle atrophy as a result of treatment with a glucocorticoid such as cortisol, dexamethasone, betamethasone, prednisone, methylprednisolone, or prednisolone;

muscle atrophy as a result of denervation due to nerve trauma or a result of degenerative, metabolic, or inflammatory neuropathy Guillian-Barre syndrome, peripheral neuropathy, or exposure to environmental toxins or drugs);

muscle atrophy as a result of myopathy, such as myotonia; a congenital myopathy, including nemalene myopathy, multi/minicore myopathy and myotubular (centronuclear) myopathy; mitochondrial myopathy; familial periodic paralysis: inflammatory myopathy; metabolic myopathy, such as caused by a glycogen or lipid storage disease; dermatomyositisis; polymyositis; inclusion body myositis; myositis ossificans; rhabdomyolysis and myoglobinurias;

myopathy caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy musculoskeletal diseases such as osteoporosis, bone fracture, short stature, or dwarfism;

adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, renal failure, congestive heart failure, ageing, space travel or time spent in a zero gravity environment.

age-related conditions such as sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, frailty, memory loss, wrinkles, impaired kidney function, and age-related hearing loss; metabolic disorders, including Type II Diabetes, Metabolic Syndrome, hyperglycemia, and obesity. Of course, patients may simultaneously suffer from one or more of these conditions, for example, sarcopenia and pulmonary emphysema, or sarcopenia and impaired kidney function.

pathological disorders such as acute and/or chronic renal disease or failure, liver fibrosis or cirrhosis, cancer such as breast cancer, Parkinson's Disease; conditions associated with neuronal death, such as ALS, brain atrophy, or dementia and anemia. In addition, there are losses suffered as a consequence of age, trauma or inactivity.

further conditions such as cachexia, cachexia associated with a rheumatoid arthritis and cachexia associated with cancer, The pharmaceutical compounds of the disclosure can also be administered in combination therapy, i.e. combined with other agents. For example, the combination therapy can include an anti-ActR2B antibody of the present disclosure combined with at least one other muscle mass/strength increasing agent, for example, IGF-1, IGF-2 or variants of IGF-1 or IGF-2, an anti-myostatin antibody, a myostatin propeptide, a myostatin decoy protein that binds ActR2B but does not activate it, a beta 2 agonist, a Ghrelin agonist, a SARM, GH agonists/mimetics or follistatin. The pharmaceutical compounds of the disclosure also can be administered in combination therapy with Nusinersen or similar compounds. Nusinersen, an antisense oligonucleotide that modulates alternate splicing of the SMN2 gene, functionally converting it into SMN1 gene, is an investigational drug for spinal muscular atrophy.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion). Depending on the route of administration, the compound of this disclosure may be coated in a material to protect the compound from the action of acids and other natural conditions that may inactivate the compound.

The compounds of the disclosure may be in the form of pharmaceutically-acceptable salts, A "pharmaceutically acceptable salt" refers to a salt that retains the desired biological activity of the parent compound and does not impart any undesired toxicological effects (see e.g. Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compounds. In addition, prolonged absorption of the injectable pharmaceutical form may be brought about by the inclusion of agents which delay absorption such as, aluminum monostearate and gelatin.

Pharmaceutically-acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compounds of the disclosure is contemplated. Supplementary active compounds can also be incorporated into the compounds.

Therapeutic compositions typically must be sterile and stable under the conditions of manufacture and storage. The compound can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the compound. Prolonged absorption of the injectable compounds can be brought about by including in the compound an agent that delays absorption for example, monostearate salts and gelatin.

Sterile injectable solutions can be prepared by incorporating the active compound in the required amount in an appropriate solvent with one or a combination of agents enumerated above, as required, followed by sterilization microfiltration. Generally, dispersions are prepared by incorporating the active compound into a sterile vehicle that contains a basic dispersion medium and the required other agents from those enumerated above. In the case of sterile powders for the preparation of sterile injectable solutions, the methods of preparation are vacuum drying and freeze-drying (lyophilization) that yield a powder of the active agent plus any additional desired agent from a previously sterile-filtered solution thereof.

The amount of compound which can be combined with a carrier material to produce a single dosage form will vary depending upon the subject being treated, and the particular mode of administration. The amount of active agent which can be combined with a carrier material to produce a single dosage form will generally be that amount of the compound which produces a therapeutic effect. Generally, out of one hundred percent, this amount will range from about 0.01 percent to about ninety-nine percent of active agent, from about 0.1 percent to about 70 percent, or from about 1 percent to about 30 percent of active agent in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compounds in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of sensitivity in individuals.

For administration of the compound, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the ranges of 1-10 mg/kg or 3-7 mg/kg. An example treatment regime entails administration once per week, once every two weeks, once every three weeks, once every four weeks, once a month, once every 3 months or once every three to 6 months. Alternatively, the compound may be administered about once a year or once only. Such administration may be carried out intravenously or subcutaneously. Dosage regimens for a compound of the disclosure include 1 mg/kg body weight or 3 mg/kg body weight by intravenous administration, with the antibody being given using one of the following dosing schedules; every four weeks for six dosages, then every three months; every three weeks; 3 mg/kg body weight once followed by 1 mg/kg body weight every three weeks.

The dosage should be one that causes an enhancement of muscle performance. In various embodiments the effect is on skeletal muscle. In various embodiments, the dosage causes muscle hypertrophy with no more than a proportional increase in the size of internal organs (e.g. heart, lungs, liver, kidneys). Such a proportional increase may be compared by measuring either mass or volume.

In some methods, two or more compounds according to this disclosure with different binding specificities may be administered simultaneously, in which case the dosage of each compound administered falls within the ranges indicated, Compound is usually administered on multiple occasions, Intervals between single dosages can be, for example, weekly, monthly, every three months, every six months or yearly. Intervals can also be irregular as indicated by measuring blood levels of compound to the target antigen in the patient. In some methods, dosage is adjusted to achieve a plasma antibody concentration of about 1-1000 mu.g/ml and in some methods about 25-300 mu.g/ml.

Alternatively, a compound can be administered as a sustained release formulation, in which case less frequent administration is required. Dosage and frequency vary depending on the half-life of the compound in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the compounds in the pharmaceutical compositions of the present disclosure may be varied so as to obtain an amount of the compound which is effective to achieve the desired therapeutic response for a particular patient, compound, and mode of administration, without being toxic to the patient. The selected dosage level will depend upon a variety of pharmacokinetic factors including the activity of the particular compounds of the present disclosure employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

A "therapeutically effective dosage" of a compound of the disclosure can result in a decrease in severity of disease symptoms, an increase in frequency and duration of disease symptom-free periods, or a prevention of impairment or disability due to the disease affliction i.e. an increase in muscle mass and/or strength.

A compound of the present disclosure can be administered by one or more routes of administration using one or more of a variety of methods known in the art. As will be appreciated by the skilled artisan, the route and/or mode of administration will vary depending upon the desired results. Routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In one embodiment the antibody is administered intravenously. In another embodiment the antibody is administered subcutaneously.

Alternatively, a compound of the present disclosure can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978.

The compounds can be administered with medical devices known in the art. For example, in one embodiment, a compound of the disclosure can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well-known implants and modules useful in the present disclosure include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art and include those made by MicroCHIPS.™. (Bedford, Mass.).

In certain embodiments, the compounds of the disclosure can be formulated to ensure proper distribution in vivo. For example, the blood-brain barrier (BBB) excludes many highly hydrophilic compounds. To ensure that the compounds of the disclosure cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g. V. V. Ranade, 1989 J. Clin Pharmacol. 29:685).

Example targeting moieties include folate or biotin (see, e.g. U.S. Pat. No. 5,416,016); mannosides (Umezawa et al., 1988 Biochem. Biophys. Res. Commun 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

A further surprising and beneficial effect of the compounds of this disclosure is that they are much more specific myostatin inhibitors than those known to the art.

It is well known that myostatin blocking agents have multiple effects, not only on muscle fibers but also on satellite cells. Satellite cells are a heterogeneous population of stem and progenitor cells that are required for the growth, maintenance and regeneration of skeletal muscle. Myostatin blocking agents switch on growth and differentiation of these muscle stem cells (McCroskery et al. (2003) J. Cell Biol, 162, 1135-1147).

Myostatin blocking agents have a different effect n muscle fibers; they switch off protein degradation of muscle filaments (responsible for muscle contraction) and turn on protein synthesis of muscle filaments (Curr Opin Support Palliat Care. 2011 Dec.; 5(4): 334-341). Myosin is the name for a family of muscle protein filaments known for their role in muscle contraction—they comprise a family of ATP-dependent motor proteins and are known for their role in muscle contraction. During muscle contraction, muscle filaments, like myosin, can be damaged and need to be degraded and replaced by new filaments. It is known that a human mutation in muscle protein degradation leads to proximal muscle weakness and hypertrophic cardiomyopathy. In a paper by Olive et al (human Molecular Genetics, 2015, 1-13) it was demonstrated that the muscle fibers of a patient contained inclusions formed by myosin and myosin-associated proteins.

Myostatin blocking agents also block protein degradation of muscle filaments and it is therefore feasible that prolonged exposure to a myostatin inhibitor leads to an accumulation of damaged muscle filaments. This could be an unwanted side effect of myostatin blocking agents such as ActR-Fc, ActRmAb and MyomAb. This may explain the relatively low activity of these proteins in performance assays such as the treadmill.

The coupling of nLG3 to ActR-Fc, ActRmAb and MyomAb described in this disclosure has resulted in novel compounds that are more specific in their mode of action. Proteins such as ActR-Fc-nLG3, ActRmAb-nLG3 and MyomAb-nLG3 activate only satellite cells and do not have a direct effect on muscle fibers. Presently, it is unclear how such proteins reach this new level of specificity in their mode of action. One explanation, without limiting the scope of this disclosure in any way, could be that Act RUB receptors use also LRP-proteins as co-receptor. It is very well known that nLG3 binds to LRP4. Binding to LRP4 is very important. The protein ActR-Fc-LG3, (note the difference between LG3 and nLG3) used as a control, leads to similar weight and muscle increase as ActR-Fc does, so the addition of a LG3 domain is not sufficient for this new activity (see FIG. 12). It is essential that the LG3 domain has an appropriate insert which makes it capable of binding to LRP4. This result also shows that a bulky residue at the C-terminus of ActR-Fc is not likely to be the reason for the novel effects of ActR-Fc-nLG3.

This disclosure therefore also provides a method of specifically activating muscle satellite cells of skeletal muscle in the absence of direct effect on muscle fibers, comprising the treatment of the muscle with a compound as hereinabove described.

The disclosure is further described with reference to the following examples and associated Figures, which depict particular embodiments and which are not in any way limiting.

A more detailed exposition of the FIGS. 1-11 is provided below, but the basic details are as follows.

Figure 11:
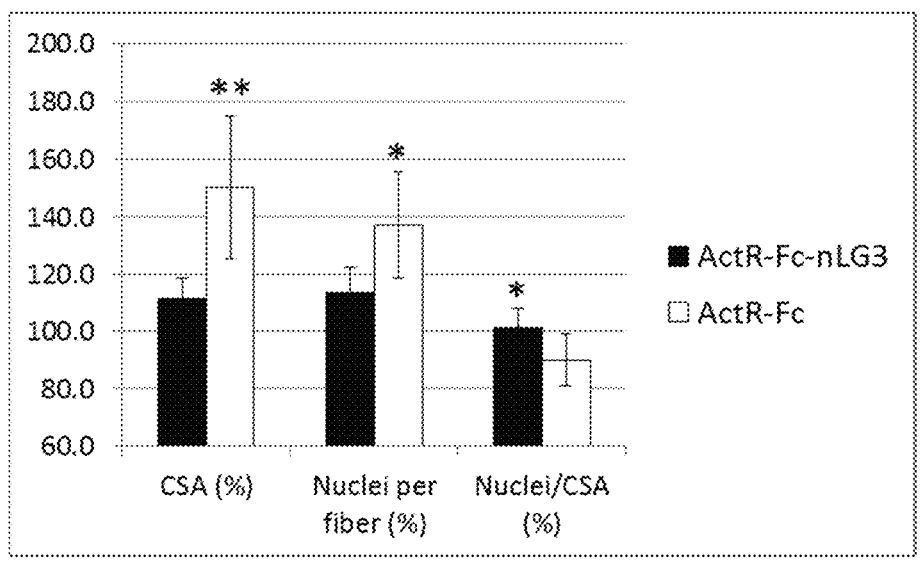

FIG. 11 Summary of muscle pathology.

Figure 12:
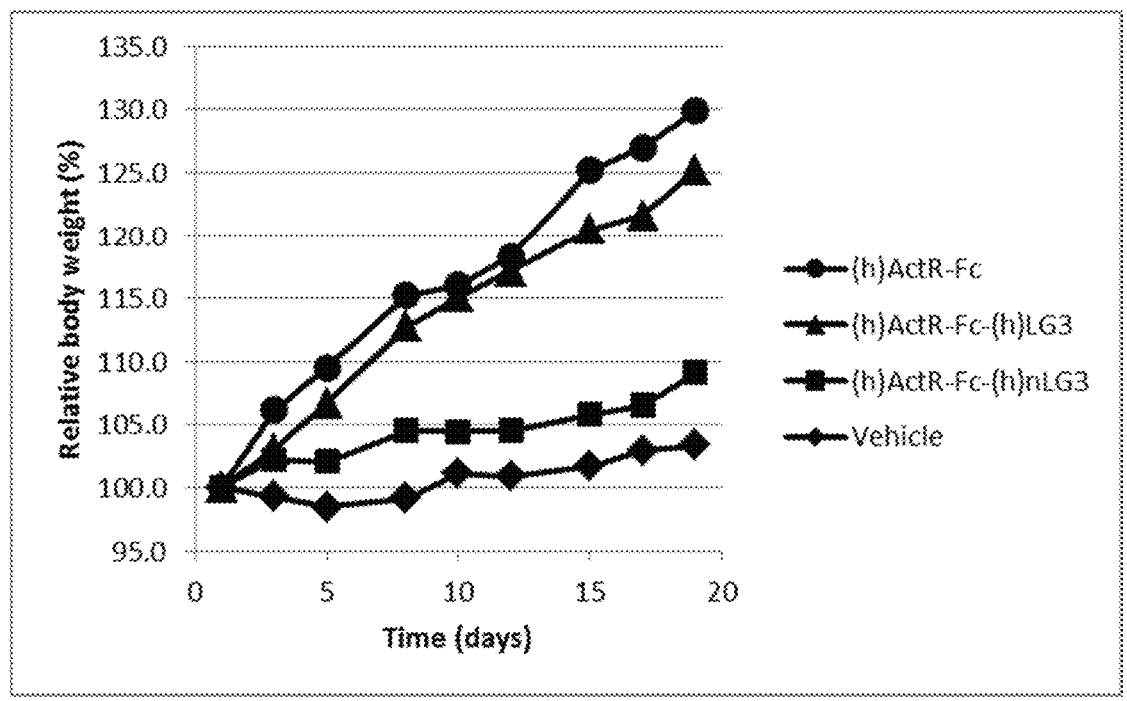

FIG. 12 shows the relative body weight increase over time.

SYNTHESIS OF PROTEINS cDNAs were obtained commercially. The cDNAs were cloned via restriction enzymes NotI and HindIII into the mammalian gene expression vector pEvi3 (evitria AG, Switzerland). Plasmid DNA was prepared under low-endotoxin conditions using commercially-available DNA purification kits (Macherey Nagel, Germany). The protein Fc-nLG3 was obtained using SEQ ID NO: 34. The protein nLG3-Fc was constructed using SEQ ID NO: 35. Fc-(h)nLG3 was constructed using SEQ ID NO: 36, Fc-(h)LG3 was constructed using SEQ ID NO: 37. Fc-ActR was constructed using SEQ ID NO: 38, ActR-Fc was constructed using SEQ ID NO: 39. (h)ActR-Fc was constructed using SEQ ID NO: 40. ActR-Fc-nLG3 was constructed using SEQ ID NO: 41.

(h)ActR-Fc-(h)nLG3 was constructed using SEQ ID NO: 42, (h)ActR-Fc-(h)LG3 was constructed using SEQ ID NO: 43, ActRmAb(LC) was constructed using SEQ ID NO: 44 and Ac1RmAb(HC) was constructed using SEQ ID NO: 45. ActRmAb(HC)-(h)nLG3 was constructed using SEQ ID NO: 46. MyomAb(LC) was constructed using SEQ ID NO: 47, and MyomAb(HC) was constructed using SEQ ID NO: 48. MyomAb(HC)-(h)nLG3 was constructed using SEQ ID NO: 49. Fol-Fc and Fol-Fc-nLG3 were constructed using SEQ ID NO: 50 and SEQ ID NO: 51 respectively.

Production and Purification of the Proteins

All proteins were produced by in CHO K1 cells. The seed was grown in eviGrow™ medium (evitria AG, Switzerland), a chemically defined, animal-component free, serum-free medium, Transfection and production were carried out in eviMake™ (evitria AG, Switzerland), an animal-component free, serum-free medium, at 37° C. and 5% CO2. ActRmAb and MyomAb are generated by simultaneous transfection with IgG heavy and light chain expression vector DNA. The resulting antibody are named ActmAb and MyomAb, respectively. ActRmAb-(h)nLG3 was made by simultaneous transfection of vector DNA generated with ActRmAb(HC)-(h)nLG3 and ActRmAb(LC). The resulting antibody is named ActmAb-(h)nLG3. MyomAb-(h)nLG3 was made by simultaneous transfection of vector DNA generated with MyomAb(HC)-(h)nLG3 and MyomAb(LC), The resulting antibody is named MyomAb-(h)nLG3.

Supernatants were harvested by centrifugation and sterile filtered (0.2 μm) at day 8 after transfection. The target proteins were subsequently purified via Protein A affinity chromatography on a Bio-Rad BioLogic DuoFlow FPLC system with PBS as wash buffer, 0.1 mol/l glycine pH 3.0 as elution buffer and 1 mol/l TRIS pH 10 as neutralization buffer.

Identification of Proteins by SDS-PAGE Gel Electrophoresis

Each compound was eluted in 4X LDS Sample Buffer (Invitrogen) and 10X reducing agent (Invitrogen) to reach the concentration of 1 μg. Samples were heated at 70° C. for 10 minutes, and subsequently run on 4-12% Bis-Tris Plus gel (Invitrogen). Gels were run at 200V voltage for 35 minutes. Target protein fractions were identified by Coomassie staining of gel. Gels were left in Coomassie staining solution (0.26% Coomassie Blue, 10% Acetic Acid, 25% Methanol) for 4 hours. After removing Coomassie solutions, gels were then incubated in the destaining solution (10% Acetic Acid, 25% Methanol) overnight, in order to eliminate the excess dye. Gels were scanned and images were taken, using a densitometer (BioRad).

Acetyl Choline Receptor Clustering on C2C12 Mouse Cells.

C2012 mouse muscle cells were cultured skeletal myoblasts from ATCC (ATCC-LGC Standards S.r.l., Italy) which were cultured in Dulbecco's Modified Eagle's Medium (DMEM) high glucose Sigma, Italy) with 10% FBS (Sigma), containing 2 mM L-glutamine, 100 U/ml penicillin and 100 μg/ml streptomycin (all purchased from Invitrogen-Gibco). They were cultured for 2-3 days on 8 well chamber slides in the previous medium, then replaced with DMEM and 3% FBS, to obtain myotubes. Myotubes were incubated with agrin constructs at 10 muM (microM) for 24 h and fixed with 2% paraformaldehyde for 20 min at RT. The samples were stained for the AChR by incubating the cells with Alexafluor 555-conjugated α-Bungarotoxin (1:500; Invitrogen, Rally) at RT for 1 h. The cells were then rinsed and coverslips were mounted with a drop of PB 0.1M. The levels of AChR clustering were compared by determining the average AChR cluster number in random fields, at a magnification of 40× with a fluorescent microscope.

Animal Studies

Ethic Statement

All procedures involving the use of laboratory animals were performed in accordance with the Italian national (DL n. 116, G.U., Supp. 40, Feb. 18, 1992; permit number 17/2010-B, Jun. 30, 2010) and European Communities Council Directive 24 Nov. 1986 (86/609/EEC).

Animals

Nine Week-Old Animals

In one experiment nine-week-old male C57BL/6 mice (n=5 per group, Harlan, Italy) were randomized with body weight and then treated subcutaneously with the proteins. The proteins used are indicated in the figures. Phosphate Buffered Saline (PBS), pH 7.4 was used as vehicle control. The dose was 10 mg/kg and is administrated three times per week, on day 1, 3, 5, 8, 10, 12 for a two week treatment. The total dose for the mixture was 20 mg/kg, consisting of a 1:1 mix of ActR-Fc and Fc-nLG3 so that each protein is given at 10 mg/kg. Body weights are determined three times per week prior to dosing 25 days after start of administration, mice are euthanized with CO2. Gastrocnemius, quadriceps femoris and triceps brachii are collected and weighed.

22 Month-Old Animals

In the aged mice experiment 24 male mice, strain C57/BL6 (purchase at Charles River, France) are used. At the beginning of the experimental procedures, mice are 22 months old, Animals are weighed, ear punched; mice are kept in regular cages, 5 per cage, under 12/12-h light/dark cycle, with food and water available ad libitum. Injections were performed subcutaneously (10 mg/kg) 3 times per week during five consecutive weeks. For the 5 week treatment the compounds were injected on day 1, 3, 5, 8, 10, 12, 15, 17, 19, 22, 24, 26, 29, 31, 33. Animals were split randomly into three experimental groups: control group (PBS), which received injections of PBS, treated groups AcrR-Fc-nLG3, and ActR-Fc.

Body Weight

Mice body weight was measured 5 times per week throughout the experiment.

Rotarod.

Rotarod measurements were done on a 7650 accelerating model of a Rotarod™ apparatus (Ugo Basile, Italy)). The mouse is placed on the rod of a Rotarod. The rod slowly accelerates from 4 to 32 rpm. The time that a mouse stays on the rod is recorded and the test terminates when the mouse is no longer able to remain on the rod. Maximum trial duration in the standard trial is 5 minutes. In the extended trial the maximum trial duration is 30 minutes. Rotarod performance of different treatment groups is indicated. Standard deviations are indicated as error bars. (N=5 for each group). The standard trial was done on day 18 and day 21 of the treatment after two exercise trials. The data is the average of four on two days. The extended trial is done on day 21 of the treatment.

Treadmill Exercise

Mice were trained on a treadmill apparatus (Panlab, Harvard Apparatus) three times per week, in the afternoon. The instrument has the capability of exercising up to five mice simultaneously in individual lanes. Mice were trained on treadmill for 3 weeks before starting compound injections, then for 3 weeks during compound/PBS dosing. Each mouse was tested using an accelerating treadmill protocol. Briefly, mice were properly acclimated to the treadmill prior to any experimentation. In the days before experimental runs, mice were placed on the treadmill in their respective lanes with shocking grids off and the belt moving and they were let to explore the instrument for minutes. During experimentation, mice were warmed up before running. For this, the belt was started at a low speed (16 cm/sec) and the shocking grids were gradually turned on to 0.2 mA. The duration of warm-up period was 2 minutes. After warm-up period, mice were tested for their running performances. The treadmill speed starts at 16 cm/sec and accelerated 1 cm every minute. The acceleration continues until the mice reach exhaustion state. If a mouse received 10 or more shock per minute, this level is considered the exhaustion state and the experiment is stopped for that particular mouse. After exhaustion, shocking grid is deactivated and the mouse is returned to its cage. The running distance, the number of shocks taken in every minute, and the total number of shocks are evaluated for each mouse.

Grip Strength Test

Forelimb grip strength was measured using a Grip Strength Meter (Ugo Basile, Varese, Italy). The control and treated mice were tested twice a week during the first six weeks of the experiments, and were tested 5 times per week in the last two weeks of experimentation. Mice were held by the tail and allowed to grasp a T-shaped bar with their forepaws. Once the mouse grasped the bar with both paws, the mouse was pulled away from the bar until the mouse released the bar. The digital meter displays the level of tension (in grams) exerted on the bar by the mouse. Each animal was given five consecutive tests, the lowest and the highest values were excluded by the analysis, and the average value was taken.

Muscle Isolation and Storage

Mice were sacrificed by cervical dislocation. After dislocation, the fresh skeletal muscles (triceps, quadriceps and gastrocnemius), were quickly dissected out from the skin and bones by forceps and scissors. The wet muscle weight was determined immediately after isolation. Then, muscles (3 for each mouse) were placed to the Peel-A-Way embedding molds (Sigma-Aldrich; E6032-1cs) containing Killik, embedding medium for criostate neutral (Bio-Optica, Milan; 05-9801), for cryosectioning. The minimal amount of Killik possible to cover the muscles was used, thus allowing rapid freezing to occur. Then the molds were immediately transferred in beaker filled with Isopentane (1-Methylbutane; Sigma-Aldrich; M32631) and dry ice (−80° C.) for 20-40 seconds (longer contact times can result in the formation of cracks in the samples; insufficient time can result in freezing artifacts) and then were transferred the muscle sample to dry ice. For long-term storage samples were kept in freezer at −80° C.

The other three muscles for each mouse were quickly placed into a tube and covered with at least 1 ml of RNAlater (Sigma-Aldrich), in order to stabilize and protect RNA with immediate RNAse inactivation. Samples were kept at 4° C. for 24 hours, then RNAlater were removed from tubes and samples were stored at −80° C. until use.

Cryosectioning

Before cryosectioning, samples were placed into the cryostat for at least 20 minutes before further processing. The sample was mounted on the round metallic mount of the cryostat with Killik embedding medium. 20 μm-thick cross sections were made and collected on warm (RT) gelatinated Superfrost slides (ThermoScientific Menzel Gläser (217655)). The sections were dried at RT for 1 hour and then stored at −20° C.

Morphometrical Analysis of Muscles

The cross-sections of mice muscles were stained with Hematoxylin Gill No. 2 (Sigma-Aldrich (GHS232)) and Eosin Y 1% aqueous solution (H/E staining procedure see). Morphometrical analysis was performed on 3 cross-sections from each experimental group. The following parameters were evaluated: 1) area and perimeter of peripherally and centrally nucleated fibers, 2) the total number of nuclei referred to the number of fibers, 3) percentage of central nuclei referred to the total number.

Data Analysis and Statistics

Data are presented as means ±S.D. (standard deviation of the mean). Student's unpaired t-test was used to determine significant differences between the experimental groups. Values of *$p<0.05$ were considered significant, $p<0.01$ very significant and *$p<0.001$ extremely significant.

The results obtained are explained with reference to the Figures.

Figure 1:
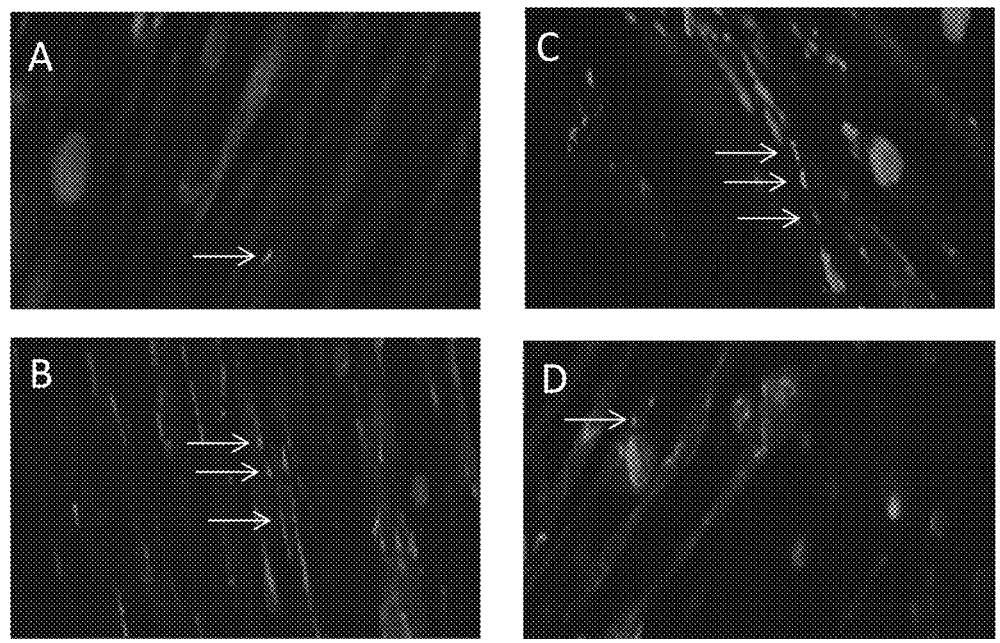
FIG. 1 shows the formation of acetyl Choline receptor clusters (dots).
Figure 2:
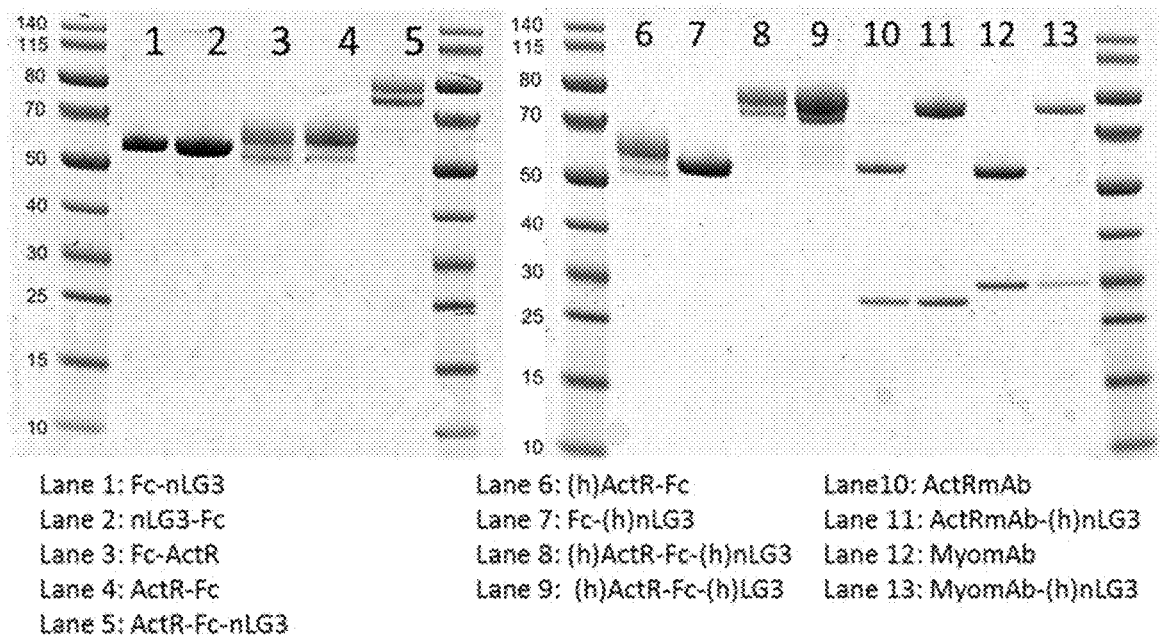
FIG. 2 shows the coomassie-stained SDS-PAGE gel of a number of compositions

FIG. 1 shows the formation of acetylcholine receptor clusters (dots), 1A, Vehicle treated control; 1B, Fc-nLG3; 1C, nLG3-Fc; 1D, ActR-Fc-nLG3. As expected at high concentration (10 muM) of Fc-agrin (1B) and agrin-Fc (1C) AChR clusters were visible. However no clear clusters were visible using ActR-Fc-nLG3 (1D) and PBS (1A). Only incidental, probably spontaneous clusters, were visible. In addition, nLG3-Fc-ActR treated cells did also not show clusters on C2C12 treated cells. (results not shown). As expected AChR clusters appeared on nLG3-Fc and Fc-nLG3 treated C2C12 cells albeit only at high concentrations. No clusters were visible at 1 muM. It is not clear why actR-Fc-nLG3 did not show AChR clusters. The "ActR" part of ActR-Fc-nLG3 might be inhibiting the formation of clusters. This might be caused by steric hindering making proper agrin binding impossible or the agrin and myostatin signaling pathways interfere, FIG. 2 shows the coomassie stained SOS-PAGE gel of: Fc-nLG3 (Lane 1); nLG3-Fc (Lane 2); Fc-ActR (Lane 3); ActR-Fc (Lane 4); ActR-Fc-nLG3 (Lane 5); (h)ActR-Fc (Lane 6); Fc-(h)nLG3 (Lane 7); (h)ActR-Fc-(h)nLG3 (Lane 8); (h)ActR-Fc-(h)LG3 (Lane 9); ActRmAb (Lane10); ActRmAb-(h)nLG3 (Lane 11); MyomAb (Lane 12); MyomAb-(h)nLG3 (Lane 13). All observed protein bands are as expected. The protein bands of ActR and (h)ActR derivatives are fuzzy because this protein is glycosylated and the degree of glycosylation generates multiple bands of the same protein.

Figure 3:
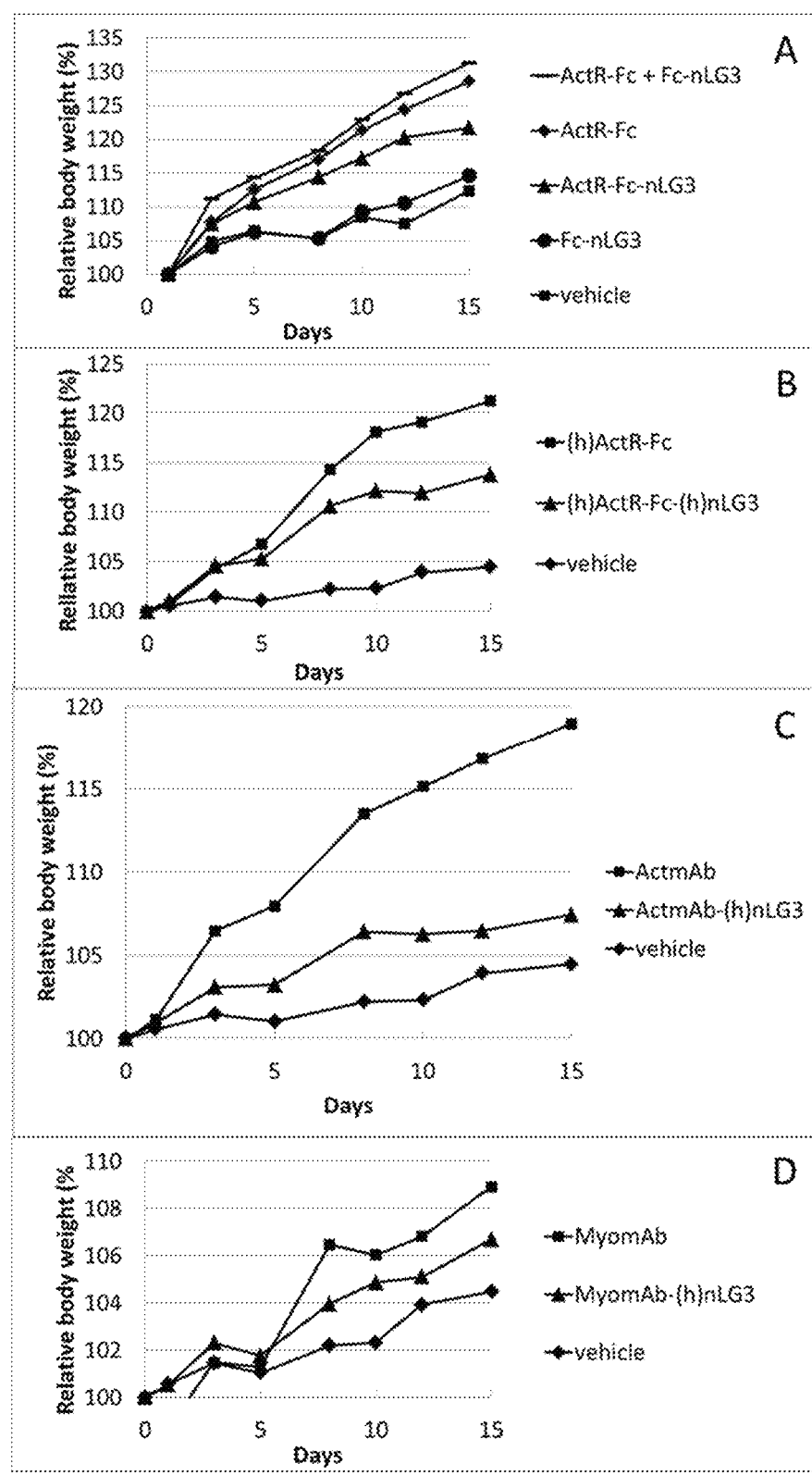
FIG. 3 shows the relative body weight increase over time.

FIG. 3 shows the relative body weight increase over time. Nine weeks old mice were treated with vehicle, ActR-Fc, Fc-nLG3, ActR-Fc-nLG3 and a 1:1 mixture of ActR-Fc and Fc-nLG3 (FIG. 2A); vehicle, (h)ActR-Fc, (h)Fc-(h)nLG3, and (h)ActR-Fc-(h)nLG3 (FIG. 2B); vehicle, ActmAb and ActmAb-nLG3 (FIG. 3C); vehicle, MyomAb and MyomAB-(h)nLG3 (FIG. 2D), As expected ActR-Fc, ActR-Fc-nLG3, and the ActR-Fc+Fc-nLG3 mixture treated mice have significantly increased body weights compared to vehicle treated mice at day15. Surprisingly, ActR-Fc-nLG3 treated mice have a significantly lower body weight compared to ActR-Fc, ActR-Fc-nLG3, and the ActR-Fc+Fc-nLG3 mixture. Also (h)Fc-(h)nLG3, ActmAb-nLG3 MyomAb-(h)nLG3 have significantly lower body weight compared to their relative control compounds (h)ActR-Fc, ActmAb and MyomAb.

Figure 4:
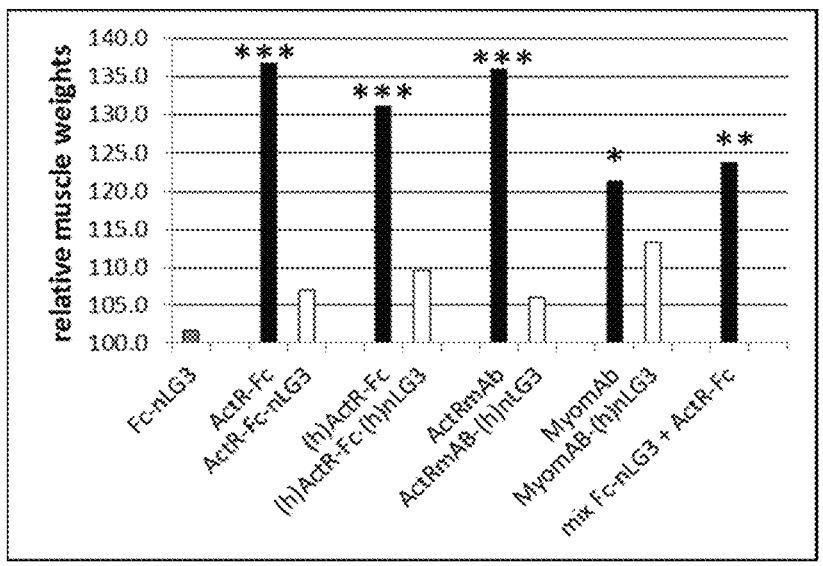
FIG. 4 shows the relative muscle weights for mice treated with vehicle and a number of compounds.

FIG. 4 shows the relative muscle weights for mice treated with vehicle, ActR-Fc, Fc-nLG3, ActR-Fc-nLG3, a 1:1 mixture of ActR-Fc, Fc-nLG3, (h)ActR-Fc, Fc-(h)nLG3, (h)ActR-Fc-(h)nLG3, ActmAb, ActmAb-nLG3, MyomAb and MyomAB-(h)nLG3. The relative mean muscle weights for the Gastrocnemius, Quadriceps and Triceps was calculated compared to muscles of vehicle treated mice. The results of the relative muscle weights resemble the results of the total body weights. As expected all compounds except Fc-nLG3 have significantly increased relative muscle weights. Surprisingly, compounds carrying in addition nLG3, or the human version of nLG3 (h)nLG3, ActR-Fc-nLG3, (h)ActR-Fc-(h)nLG3 ActmAb-(h)nLG3 MyomAb-(h)nLG3 have significantly lower body weights compared to their control compounds.

Figure 5:
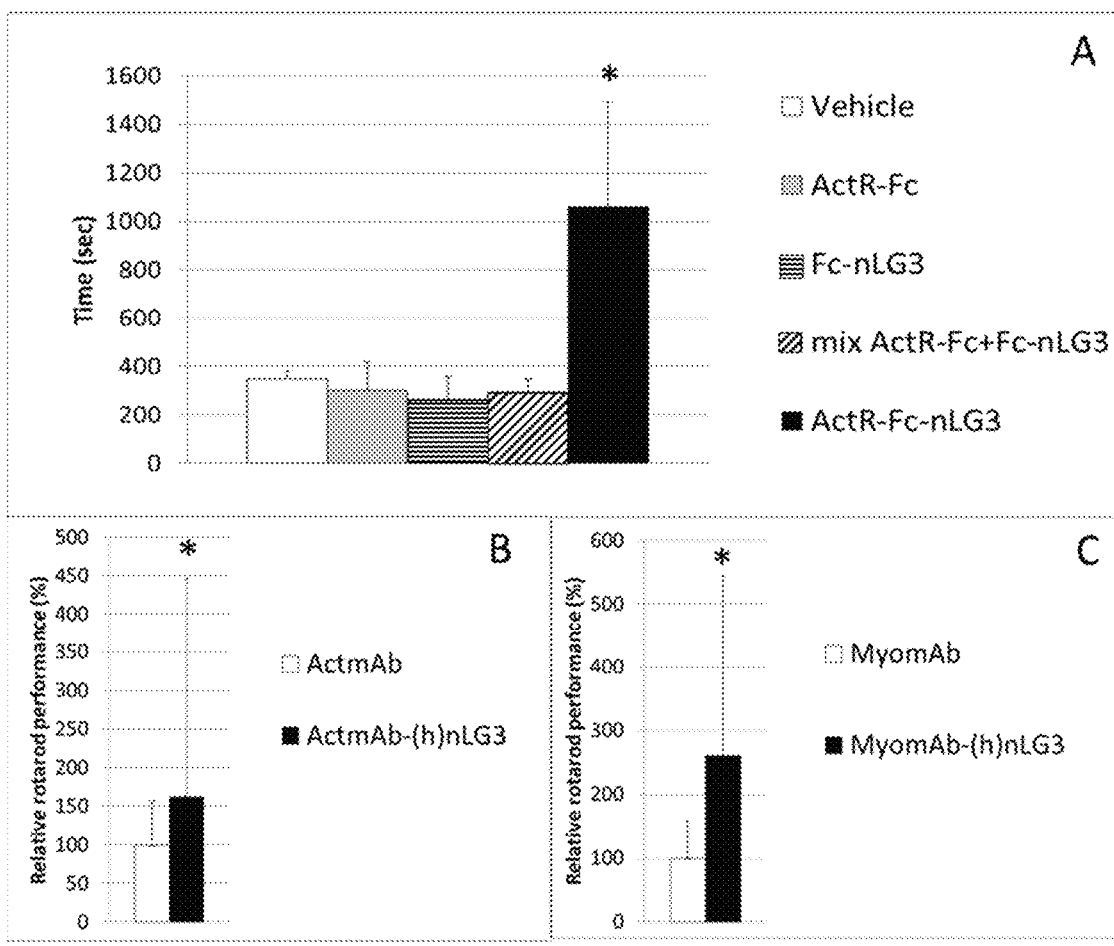
FIG. 5 shows the rotarod performance of treated mice.

FIG. 5 shows the rotarod performance of the mice. The performance of ActR-Fc, Fc-nLG3, a 1:1 mixture of ActR-Fc and Fc-nLG3, ActmAb, MyomAb treated mice were not significantly increased. Surprisingly, the performance of the nLG3 resp (h)nLG3 containing compounds ActR-Fc-nLG3, ActmAb-nLG3 and MyomAB-(h)nLG3 were significantly increased compared to their control compounds ActR-Fc, ActmAb, MyomAb.

Figure 6:
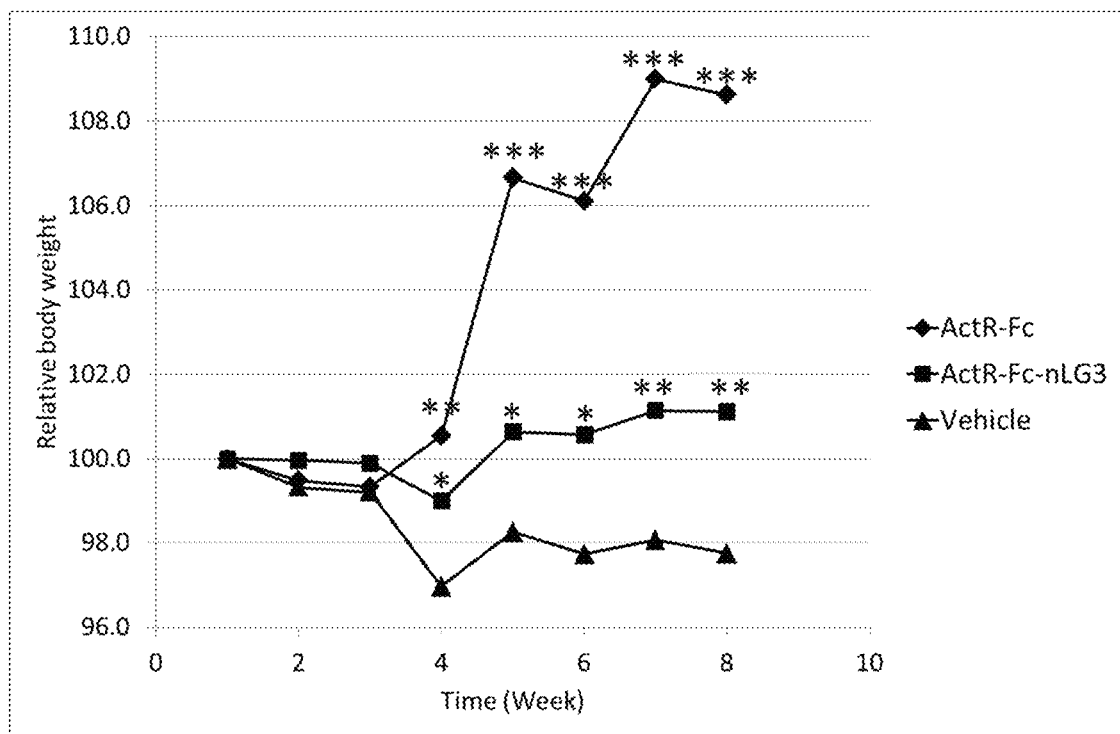
FIG. 6 shows relative body weight increase over time.

FIG. 6 shows the relative body weight increase over time. The relative mean body weight for every week was calculated. All 22 old mice were treated with vehicle (PBS) during the first three weeks of the experiment. In the following five weeks the aged mice were treated with vehicle, ActR-Fc, and ActR-Fc-nLG3. After week 3 the ActR-Fc dosed animals reach highly significant levels of weight increased compared to vehicle. After week 3 ActR-Fc-nLG3 dosed animals have significantly increased body weight compared to vehicle but significantly lower than the body weights of ActR-Fc.

Figure 7:
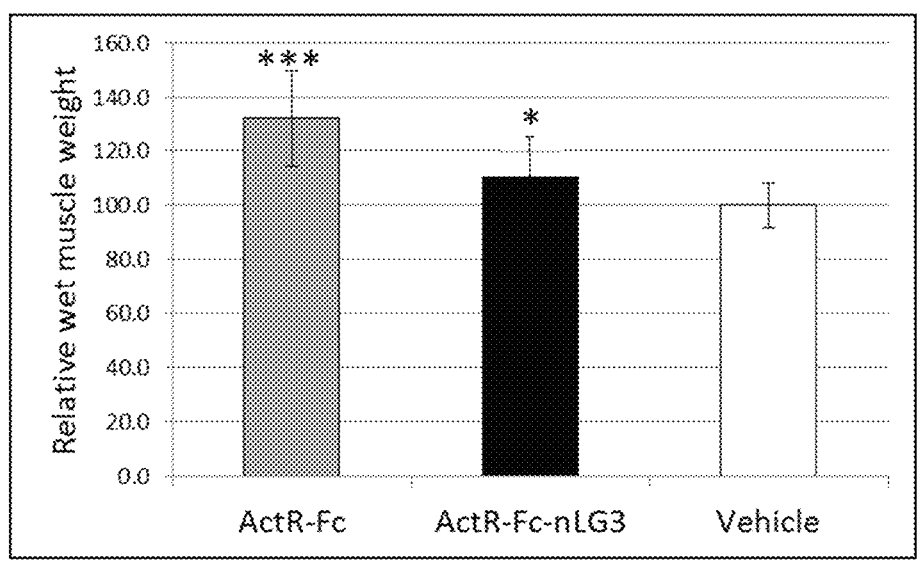
FIG. 7 shows relative muscle wet weights.

FIG. 7 shows the relative muscle wet weights. The relative mean muscle weights for the Gastrocnemius, Quadriceps and Triceps was calculated compared to muscles of vehicle treated mice. ActR-Fc dosed animals have highly significant levels of muscle weight increased compared to vehicle. ActR-Fc-nLG3 dosed animals are significantly increased in muscle weight compared to vehicle but significantly lower than the body weights of ActR-Fc.

Figure 8:
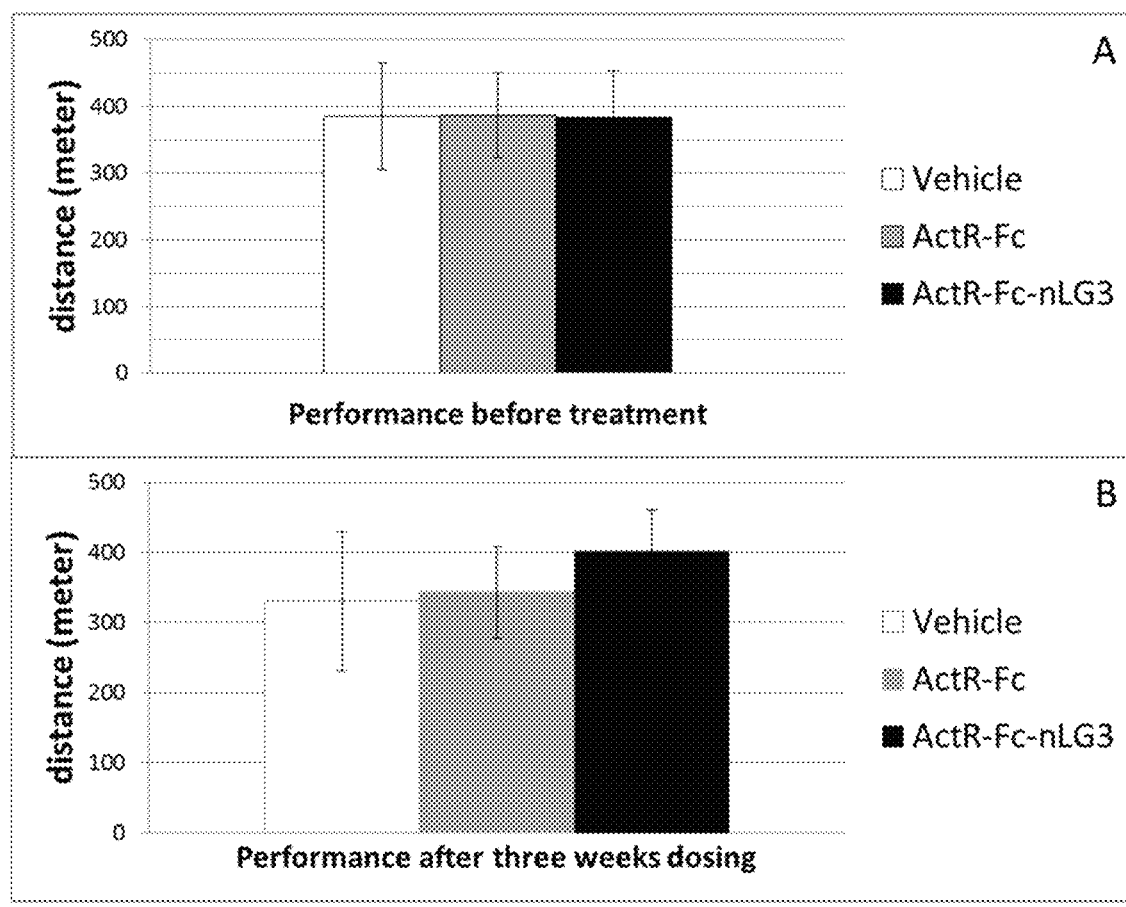
FIG. 8 shows the treadmill performance of the aged mice.

FIG. 8 shows the treadmill performance of the aged mice, FIG. 8A shows the treadmill performance during week three of vehicle dosing (before treatment). At this time point the performances of all groups are very similar. FIG. 8B shows the mean treadmill performance during week 5 and 6 (after treatment). The performance of ActR-Fc and vehicle treated mice were lower after treatment than before treatment (not significant). It is likely that with increasing age the treadmill performance of these mice is declining. Surprisingly, the performance of ActR-Fc-nLG3 treated mice was improved after treatment compared to before treatment (p=X). This shows that in spite of the mice being older, the treadmill performance improved. The performance of ActR-Fc-nLG3 in treated mice was significantly higher than vehicle and ActR-Fc treated mice. This shows that treatment with ActR-Fc-nLG3 improves the muscle endurance of the aged mice.

Figure 9:
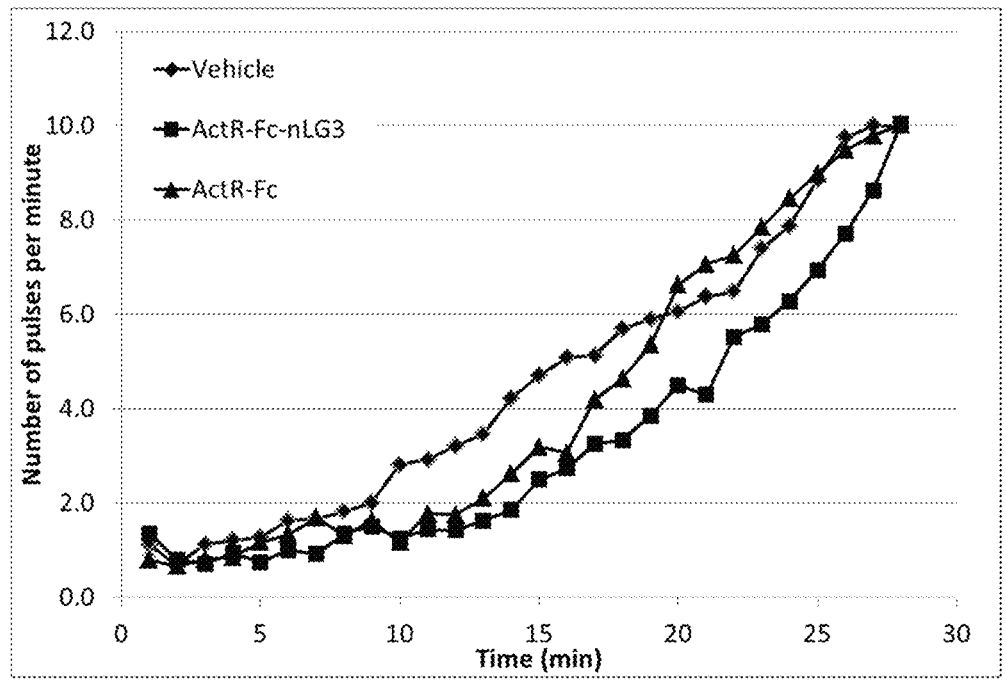
FIG. 9 shows the number of motivational electrical pulses per minute during the treadmill runs.

FIG. 9 shows the mean number of motivational electrical pulses per minute during the treadmill runs at week 5 and 6. Mice require more electrical pulses when they get exhausted. ActR-Fc and vehicle treated mice needed more pulses then ActR-Fc-nLG3 treated mice. This was highly significant $p<0.001$. Interestingly, in the first nine minutes all three groups of mice required about the same number of pulses with no statistical differences. With increasing time on the treadmill, the performance of ActR-Fc-nLG3 treated mice was much better and the mice required fewer pulses than vehicle and ActR-Fc treated mice. This also clearly shows that mice treated with ActR-Fc-nLG3 have improved muscle endurance.

Figure 10:
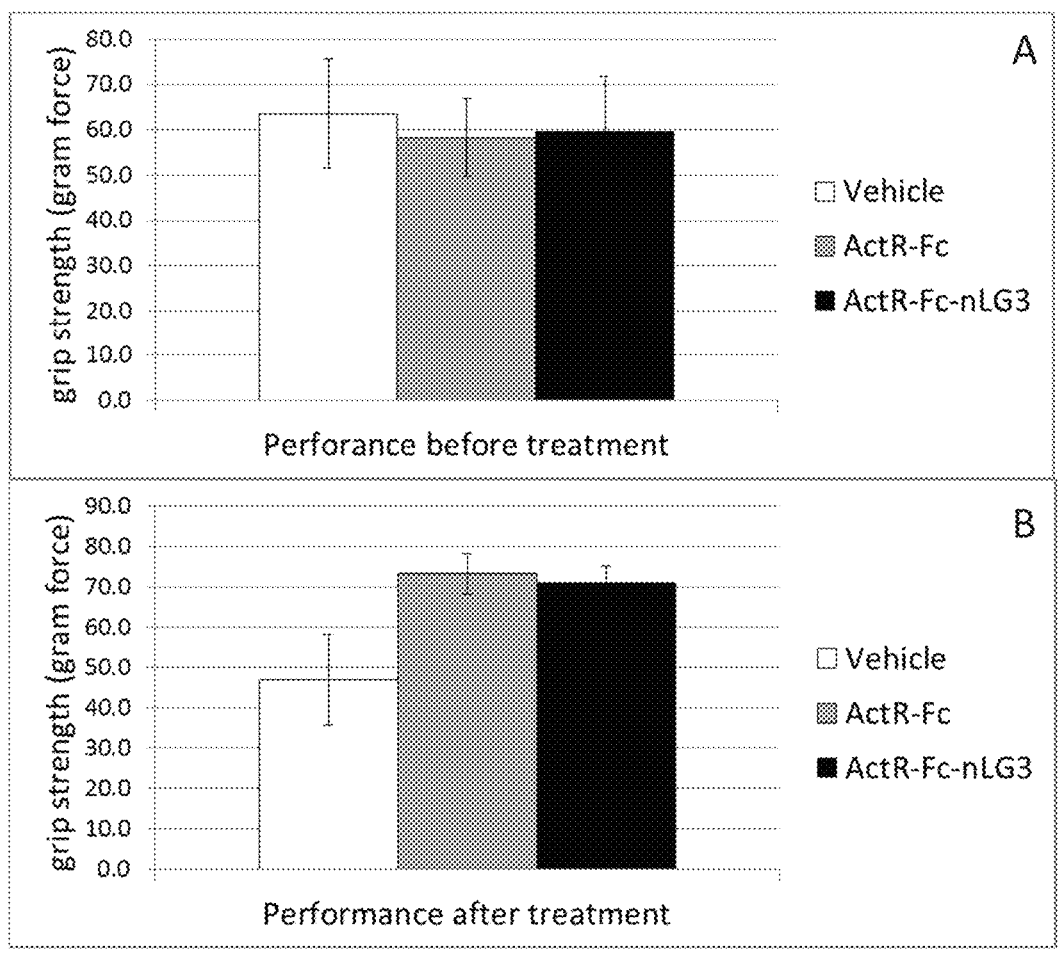
FIG. 10 shows the mean grip strength (GS) performance of the mice during week three of vehicle dosing (GS before treatment).

FIG. 10 shows the mean grip strength (GS) performance of the mice during week three of vehicle dosing (GS before treatment). At this time point the performances of all groups are very similar. FIG. 7B shows the mean grip strength (GS) performance during week 5 and 6 (GS after treatment). The performance of vehicle treated mice was lower after treatment than before treatment (significant). The performance of ActR-Fc and ActR-Fc-nLG3 treated mice were higher after treatment then before treatment (significant). The GS performance of ActR-Fc-nLG3 and ActR-Fc treated mice were very similar after treatment and both are significantly increased compared to vehicle treated mice. So administration of the compound ActR-Fc-nLG3 has retained the increased muscle strength performance as ActR-Fc.

FIG. 11 Summary of muscle pathology. Cross sectional area (CSA), and number of nuclei per muscle fiber were determined for vehicle, ActR-Fc and ActR-Fc-nLG3 treated mice. From these results, the number of nuclei per CSA was calculated. In FIG. 11 the relative values for CSA, and number of nuclei per nuclei per fiber and number of nuclei per CSA are depicted. ActR-Fc ($p<0.001$) and ActR-Fc-nLG3 ($p<0.05$) treated mice have a statistically significantly increased CSA and number of nuclei per fiber compared to vehicle treated mice. In addition, compared to ActR-Fc-nLG3, ActR-Fc treated mice have a significantly increased CSA ($p<0.01$) and number of nuclei ($p<0.05$). However, compared to vehicle or ActR-Fc-nLG3, ActR-Fc treated mice have a significantly decreased number of nuclei per fiber area ($p<0.05$). Nuclei formation is promoted by the activity of the satellite cells. As satellite cells grow and differentiate they will fuse with an existing muscle fiber leading to more nuclei the muscle fiber.

FIG. 12 shows the relative body weight increase over time. Nine weeks old mice were treated with vehicle, (h)ActR-Fc, (h)ActR-Fc-(h)nLG3, and (h)ActR-Fc-(h)LG3. At day 19 ActR-Fc, (h)ActR-Fc-(h)nLG3, and (h)ActR-Fc-(h)LG3 treated mice have significantly increased relative body weights ($p<0.001$, $p<0.05$, $p<0.001$ respectively) compared to vehicle treated mice. The relative body weights of (h)ActR-Fc-(h)LG3 and (h)ActR-Fc are not significantly different. Notably, (h)ActR-Fc-(h)LG3 treated mice have a significantly ($p>0.01$) higher body weight compared to (h)ActR-Fc-(h)nLG3. The two proteins differ only by an 8 amino acid sequence insert in (h)nLG3. This insert is responsible for binding to the LRP4 receptor, so (h)nLG3 binds to the LRP4 receptor whereas (h)LG3 does not bind. Mice treated with (h)ActR-Fc-(h)nLG3 show a similar growth curve as ActR-Fc-nLG3 (FIG. 3).

From these results it seems likely that muscle growth of ActR-Fc-nLG3 is solely caused by growth of muscle stem cells, (i.e. satellite cells) which fuse with the muscle fiber leading to more nuclei. More nuclei will lead to higher protein synthesis in the muscle fiber leading to a modest increase in muscle and body weight increase in ActR-Fc-nLG3, (h)ActR-Fc-(h)nLG3. ActRmAb-nLG3 and MyomAb-nLG3 treated animals. Treatment with ActR-Fc also leads to more nuclei but the fiber growth is over proportional leading in fact to a lower nuclei density.

The invention claimed is:

1. A compound comprising a C-terminal nLG3 or (h)nLG3 domain of mouse or human agrin joined via a linker to a protein or an antibody, wherein the compound is selected from at least one of:
   i) the protein ActR-Fc comprising SEQ ID NO: 19 linked to the nLG3 domain comprising SEQ ID NO: 5,
   ii) the protein (h)ActR-Fc comprising SEQ ID NO: 21 linked to the (h)nLG3 domain comprising SEQ ID NO: 10,
   iii) the protein Fol-Fc comprising SEQ ID NO: 26 linked to the nLG3 domain comprising SEQ ID NO: 5,
   iv) the antibody comprising the light chain sequence comprising SEQ ID NO: 29 (ActRmAb(LC)) and the heavy chain sequence comprising SEQ ID NO: 28 (ActRmAb(HC)) linked to the (h)nLG3 domain comprising SEQ ID NO: 10,
   v) the antibody comprising the light chain sequence comprising SEQ ID NO: 32 (MyomAb(LC)) and the heavy chain sequence comprising SEQ ID NO: 31 ((MyomAb(HC)) linked to the (h)nLG3 domain comprising SEQ ID NO: 10.

2. A method of improving muscle performance, comprising the administration of an effective amount of a compound according to claim 1.

3. A pharmaceutical composition comprising at least one compound according to claim 1, formulated together with a pharmaceutically-acceptable carrier.

4. A method of treatment of the loss of muscle function resulting from a pathological condition, comprising the administration of an effective amount of the compound according to claim 1.

* * * * *